US008408209B2

(12) United States Patent
Matsubara et al.

(10) Patent No.: US 8,408,209 B2
(45) Date of Patent: Apr. 2, 2013

(54) PRESSURE CONTROLLER FOR ARTIFICIAL RESPIRATOR AND ARTIFICIAL RESPIRATOR USING THE SAME

(75) Inventors: Terumi Matsubara, Tokyo (JP); Toshio Otomo, Saitama (JP); Yutaka Sekiguchi, Saitama (JP); Takashi Tanabe, Saitama (JP); Kazuo Matsubara, Tokyo (JP)

(73) Assignee: Atom Medical Corporation, Tokyo (JP)

( * ) Notice: Subject to any disclaimer, the term of this patent is extended or adjusted under 35 U.S.C. 154(b) by 609 days.

(21) Appl. No.: 12/686,101

(22) Filed: Jan. 12, 2010

(65) Prior Publication Data
US 2010/0206310 A1 Aug. 19, 2010

(30) Foreign Application Priority Data

Feb. 16, 2009 (JP) .................................. 2009-32371

(51) Int. Cl.
*A62B 9/02* (2006.01)
(52) U.S. Cl. ......... 128/205.24; 128/205.25; 128/204.17; 128/204.18
(58) Field of Classification Search ............. 128/204.17, 128/204.18, 205.24, 205.25
See application file for complete search history.

(56) References Cited

U.S. PATENT DOCUMENTS
6,644,313 B2 11/2003 Prime et al.

*Primary Examiner* — Laura Bouchelle
(74) *Attorney, Agent, or Firm* — Hunton & Williams LLP

(57) ABSTRACT

A pressure controller for an artificial respirator according to this invention includes a control valve facing a gas passage between an inspiratory gas inlet and an inspiratory gas outlet, and an elastic biasing means for elastically biasing the control valve against a valve seat. When an adjustment manipulating member moves backward, even the pivotal motion of the adjustment manipulating member does not operate an adjustment operating member. When the adjustment manipulating member is pulled out, the pivotal motion of the adjustment manipulating member operates the adjustment operating member, thereby adjusting the elastic biasing force of the elastic biasing means. This invention provides a pressure controller for an artificial respirator capable of reliably preventing unnecessary operating of the adjustment operating member although the pivoting operation of the adjustment manipulating member is simple as a whole, and there is no possibility that the adjustment manipulating member and the like are broken.

23 Claims, 16 Drawing Sheets

PRESSURE CONTROLLER FOR ARTIFICIAL RESPIRATOR AND ARTIFICIAL RESPIRATOR USING THE SAME

CROSS-REFERENCE TO RELATED APPLICATIONS

This application claims benefit of the Japanese Patent Application No. 2009-32371, entitled "Pressure Controller for Artificial Respirator and Artificial Respirator Using the Same," filed on Feb. 16, 2009, the entire content of which is hereby incorporated by reference.

TECHNICAL FIELD

The present invention relates to a pressure controller for use in an artificial respirator such as a resuscitator for supplying a gas to a patient requiring respiratory assistance, comprising a housing mechanism which has a first vent hole, a second vent hole and a third vent hole, and in which one of the first vent hole and the second vent hole is configured to be used as an inlet of an inspiratory gas and the other vent hole is configured to be used as an outlet of the inspiratory gas, a control valve placed in the housing mechanism to face a gas passage between the first vent hole and the second vent hole, elastic biasing means for elastically biasing the control valve against a valve seat formed in the housing mechanism, an adjustment operating member to be operated to adjust an elastic biasing force of the elastic biasing means, and an adjustment manipulating member to be pivoted to operate the adjustment operating member, wherein the control valve closes the third vent hole when a gas pressure in the gas passage is lower than a predetermined level, and the control valve opens the third vent hole such that a gas in the gas passage flows through the third vent hole when the gas pressure in the gas passage is higher than a predetermined level. The present invention also relates to an artificial respirator configured to control the gas pressure by the pressure controller as described above.

BACKGROUND OF THE INVENTION

A pressure controller for use in an artificial respirator for supplying a gas to a patient requiring respiratory assistance is disclosed in, e.g., U.S. Pat. No. 6,644,313B2. This pressure controller (to be referred to as "the pressure controller of patent reference" hereinafter) disclosed in U.S. Pat. No. 6,644,313B2 includes a housing mechanism having an inspiratory gas inlet, inspiratory gas outlet and third vent hole. The pressure controller of patent reference further includes:

(a) a control valve placed in a substantially cylindrical valve housing of the housing mechanism so as to face a gas passage between the inspiratory gas inlet and inspiratory gas outlet, (b) a coil spring for elastically biasing the control valve against a valve seat formed in the valve housing, and (c) an adjustment manipulating cap to be rotated to adjust the elastic biasing force of the coil spring.

The adjustment manipulating cap is screwed into a threaded portion formed on the outer circumferential surface of the tubular portion of the valve housing. Also, a gas discharge hole is formed as the third vent hole in the tubular portion of the valve housing. The control valve opens or closes in accordance with the pressure of a gas flowing through the gas passage, and the amount of screw-tightening or screw-loosening of the adjustment manipulating cap with respect to the threaded portion. Therefore, the gas flowing through the gas passage partially flows outside from the gas discharge hole in accordance with this open/closure state. In addition, to prevent an unnecessary pivotal motion of the adjustment manipulating cap, a pivotal-motion-preventing locking cap is detachably fitted on the cylindrical portion so as to cover the adjustment manipulating cap.

In the pressure controller of patent reference configured as described above, however, the adjustment manipulating cap must be covered with the pivotal-motion-preventing locking cap in order to prevent an unnecessary pivotal motion of the adjustment manipulating cap when, e.g., an operator or the like touches the cap with fingers. Also, to tighten or loosen the adjustment manipulating cap, the pivotal-motion-preventing locking cap must be removed from the adjustment manipulating cap. This increases the number of parts because the pivotal-motion-preventing locking cap is additionally necessary. In addition, the adjustment manipulating cap must be pivoted after the pivotal-motion-preventing locking cap is removed, and the pivotal-motion-preventing locking cap must be reattached after this pivotal motion. This complicates the pivoting operation of the adjustment manipulating cap as a whole. Also, the adjustment manipulating cap may unnecessarily pivot when removing and attaching the pivotal-motion-preventing locking cap. Furthermore, an operator may lose the pivotal-motion-preventing locking cap or may forget to attach it. Accordingly, the pressure controller of patent reference has the problem in reliably preventing an unnecessary pivotal motion of the adjustment manipulating cap.

SUMMARY OF THE INVENTION

The present invention can effectively correct the drawbacks of the pressure controller of patent reference as described above with a relatively simple arrangement.

According to the first aspect of the present invention, the present invention is a pressure controller for use in an artificial respirator such as a resuscitator for supplying a gas to a patient requiring respiration assistance, comprising a housing mechanism which has a first vent hole, a second vent hole and a third vent hole, and in which one of the first vent hole and the second vent hole is configured to be used as an inlet of an inspiratory gas and the other vent hole is configured to be used as an outlet of the inspiratory gas, a control valve placed in the housing mechanism to face a gas passage between the first vent hole and the second vent hole, elastic biasing means for elastically biasing the control valve against a valve seat formed in the housing mechanism, an adjustment operating member to be operated to adjust an elastic biasing force of the elastic biasing means, and an adjustment manipulating member to be pivoted to operate the adjustment operating member, wherein the control valve closes the third vent hole when a gas pressure in the gas passage is lower than a predetermined level, and the control valve opens the third vent hole such that a gas in the gas passage flows through the third vent hole when the gas pressure in the gas passage is higher than a predetermined level, characterized in that the adjustment operating member does not operate even when the adjustment manipulating member pivots by a pivoting operation of the adjustment manipulating member in a first state in which the adjustment manipulating member moves backward to the adjustment operating member, and the adjustment operating member operates to adjust the elastic biasing force of the elastic biasing means when the adjustment manipulating member pivots by the pivoting operation of the adjustment manipulating member in a second state in which the adjustment manipulating member is pulled out from the adjustment operating member. In this configuration of the first aspect (the second aspect to be described later is the same}, the adjustment manipulating member need not be covered with any pivotal motion preventing locking cap in order to prevent an unnecessary pivotal motion of the adjustment manipulating member. This simplifies the pivoting operation of the adjustment manipulating member as a whole. Also, there is no problem in reliably preventing unnecessary operating of the adjustment operating member. Furthermore, when the adjustment manipulating member moves backward to the adjustment operating member, the adjustment operating member does not operate even if the adjustment manipulating member pivots by the pivoting operation of the adjustment manipulating member. Accordingly, the adjustment manipulating member is not pivoted by a very large force unlike when the pivotal motion of the adjustment manipulating member is forcedly inhibited. This protects the adjustment manipulating member, adjustment operating member and the like from being broken.

According to the first mode of the first aspect of the present invention, a rotational torque required to pivot the adjustment manipulating member in the first state is preferably 4 to 25 cN*m (more preferably, 5 to 20 cN–m, and most preferably, 7 to 15 cN–m). In this configuration of the first mode of the first aspect (the fourth mode of the first aspect to be described later is the same), in the first state in which the adjustment manipulating member moves backward to the adjustment operating member and the adjustment operating member does not operate even when the adjustment manipulating member pivots by the pivoting operation of the adjustment manipulating member, the rotational torque required to pivot the adjustment manipulating member is relatively high. Accordingly, an operator such as a doctor has neither a sense of unease nor a sense of incompatibility when handling the adjustment manipulating member in the first state.

According to the second mode of the first aspect of the present invention, a rotational torque required to pivot the adjustment manipulating member in the second state is preferably 1.5 to 10 cN*m (more preferably, 2 to 8 cN–m, and most preferably, 3 to 6 cN–m). In this configuration of the second mode of the first aspect (the fifth mode of the first aspect to be described later is the same), in the second state in which the adjustment manipulating member is pulled out from the adjustment operating member and the adjustment operating member operates to adjust the elastic biasing force of the elastic biasing means when the adjustment manipulating member pivots by the pivoting operation of the adjustment manipulating member, the rotational torque required to pivot the adjustment manipulating member is high to some extent. Accordingly, an operator such as a doctor has neither a sense of unease nor a sense of incompatibility when handling the adjustment manipulating member in the second state. In addition, it is easy to accurately perform fine adjustment of the elastic biasing force of the elastic biasing means.

According to the third mode of the first aspect of the present invention, a ratio of the rotational torque required to pivot the adjustment manipulating member in the first state to the rotational torque required to pivot the adjustment manipulating member in the second state is preferably 1.2 to 5 (more preferably, 1.6 to 4, and most preferably, 2 to 3). According to the third mode of the first aspect described above, the rotational torque required to pivot the adjustment manipulating member in the first state is higher than that in the second state. In the first state, therefore, the adjustment manipulating member is not pivoted by an operation error. In addition, it is possible to well perform adjustment and fine adjustment of the adjustment manipulating member in the second state.

According to the fourth mode of the first aspect of the present invention, the present invention is preferably configured such that a first three-dimensional engaging portion is formed on a side of the housing mechanism, a second three-dimensional engaging portion configured to engage with the first three-dimensional engaging portion is formed on a side of the adjustment manipulating member, and engagement of the first three-dimensional engaging portion and the second three-dimensional engaging portion in the first state increases the rotational torque required to pivot the adjustment manipulating member. According to the fifth mode of the first aspect obtained by extending the fourth mode of the first aspect described above, the present invention is preferably configured such that engagement of the first three-dimensional engaging portion and the second three-dimensional engaging portion in the second state increases the rotational torque required to pivot the adjustment manipulating member. According to the sixth mode of the first aspect of the present invention obtained by extending the fourth mode of the first aspect described above, the first three-dimensional engaging portion is preferably a three-dimensional engaging portion formed into a substantially ring shape on an outer circumferential surface of the housing mechanism, and the second three-dimensional engaging portion comprises a plurality of three-dimensional engaging portions intermittently formed on an inner circumferential surface of the adjustment manipulating member. In this configuration of the sixth mode of the first aspect, the pivotal torque required to pivot the adjustment manipulating member with respect to a side of the housing mechanism can reliably be increased with a relatively simple arrangement.

According to the seventh mode of the first aspect, the present invention preferably comprises a top-surface member attached to a side of the housing mechanism such that the top-surface member does not move forward and backward in the direction in which the adjustment manipulating member is pulled out, and a conical coil spring interposed between the top-surface member and the adjustment manipulating member, wherein the adjustment manipulating member moving forward in the direction in which the adjustment manipulating member is pulled out is elastically biased in a direction of the backward motion by the conical coil spring. In this configuration of the seventh mode of the first aspect, in the second state in which the adjustment manipulating member is pulled out from the adjustment operating member, the adjustment manipulating member automatically moves backward by the elastic biasing force of the conical coil spring when an operator such as a doctor releases fingers from the adjustment manipulating member after pivoting the adjustment manipulating member with the fingers. This makes it possible to relatively easily perform the adjusting operation by the adjustment manipulating member. In addition, the conical coil spring is interposed between the top-surface member and adjustment manipulating member in order to automatically move the adjustment manipulating member backward. Accordingly, the accommodation space of the spring can be narrowed.

According to the eighth mode of the first aspect, the present invention is preferably configured such that the adjustment operating member comprises a first adjustment operating member arranged in the housing mechanism, and a second adjustment operating member arranged in the housing mechanism, the first adjustment operating member is configured to pivot by the pivoting operation of the adjustment manipulating member, thereby pivoting the second adjustment operating member, and the second adjustment operating member operates by the pivotal motion to adjust the elastic biasing force of the elastic biasing means. In this configuration of the eighth mode of the first aspect, the pivoting operation of the adjustment manipulating member pivots the first adjustment operating member, and the second adjustment operating member operates by this pivotal motion of the first adjustment operating member to adjust the elastic biasing force of the elastic biasing means. This makes it possible to reliably and smoothly perform the operation of adjusting the state in which the control valve is urged against the valve seat. According to the ninth mode of the first aspect of the present invention obtained by extending the eighth mode of the first aspect described above, the adjustment manipulating member is preferably an adjustment manipulating cap, and the adjustment manipulating cap is preferably substantially put on a head of the first adjustment operating member. In this configuration of the ninth mode of the first aspect, the adjustment manipulating member can easily and reliably be pivoted with respect to the first adjustment operating member. In addition, an interlocking/uninterlocking mechanism that transmits or does not transmit the pivotal motion of the adjustment manipulating member to the first adjustment operating member can simply and reliably be formed between the first adjustment operating member and adjustment manipulating member.

According to the 10th mode of the first aspect, the present invention is preferably configured such that the adjustment manipulating member comprises a first pivotal-motion-transmitting engaging portion, the adjustment operating member comprises a second pivotal-motion-transmitting engaging portion, and when the adjustment manipulating member is in a backward-motion position in which the adjustment manipulating member moves backward to the adjustment operating member, the first pivotal-motion-transmitting engaging portion of the adjustment manipulating member and the second pivotal-motion-transmitting engaging portion of the adjustment operating member are disengaged, and the adjustment operating member does not operate even when the adjustment manipulating member pivots by the pivoting operation of the adjustment manipulating member, and, when the adjustment manipulating member is pulled out from the backward-motion position with respect to the adjustment operating member, the first pivotal-motion-transmitting engaging portion and the second pivotal-motion-transmitting engaging portion engage with each other, thereby transmitting the pivoting operation of the adjustment manipulating member to the adjustment operating member and operating the adjustment operating member. In this configuration of the 10th mode of the first aspect, the arrangement of an interlocking/uninterlocking mechanism for achieving transmission or non-transmission of the pivotal motion of the adjustment manipulating member to the adjustment operating member can be simplified, and the operation can reliably be performed. According to the 11th mode of the first aspect of the present invention, an opening communicating with the third vent hole is preferably formed in a top-surface portion of the adjustment manipulating member. In this configuration of the 11th mode of the first aspect, an operator can control the number of times of respiration of a patient by intermittently closing the opening formed in the top-surface portion of the adjustment manipulating member with a finger or the like. In addition, even if the operator strongly presses the top-surface portion of the adjustment manipulating member when closing the opening with his or her finger, the adjustment manipulating member idles with respect to the adjustment operating member. Therefore, the adjustment operating member does not unnecessarily operate.

According to the second aspect of the present invention, the present invention relates to an artificial respirator configured to control a gas pressure by the pressure controller according to the first aspect described above. According to the first mode of the second aspect, the present invention preferably further comprises a face mask including a second inspiratory gas inlet to be connected to the inspiratory gas outlet of the pressure controller, wherein both the first vent hole and the second vent hole of the pressure controller are configured to be selectively connected to the second inspiratory gas inlet of the face mask, and one of the first vent hole and the second vent hole having connected to the second inspiratory gas inlet functions as the inspiratory gas outlet of the pressure controller, and the other vent hole functions as the inspiratory gas inlet of the pressure controller. In this configuration of the first mode of the second aspect, an operator of the pressure controller can use the pressure controller in two use states. Therefore, the operator can use the pressure controller in a use state convenient for him or her. According to the second mode of the second aspect of the present invention, an angle which an axis of the first vent hole of the pressure controller makes with an axis of the second vent hole is preferably 75° to 105° (more preferably, 80° to 100°, and most preferably, 85° to 95°). In this configuration of the second mode of the second aspect, the pressure controller can relatively conveniently be used in either of the two use states described above.

The above, and other, objects, features and advantages of this invention will become readily apparent from the following detailed description thereof which is to be read in connection with the accompanying drawings.

DETAILED DESCRIPTION OF THE INVENTION

Figure 1:
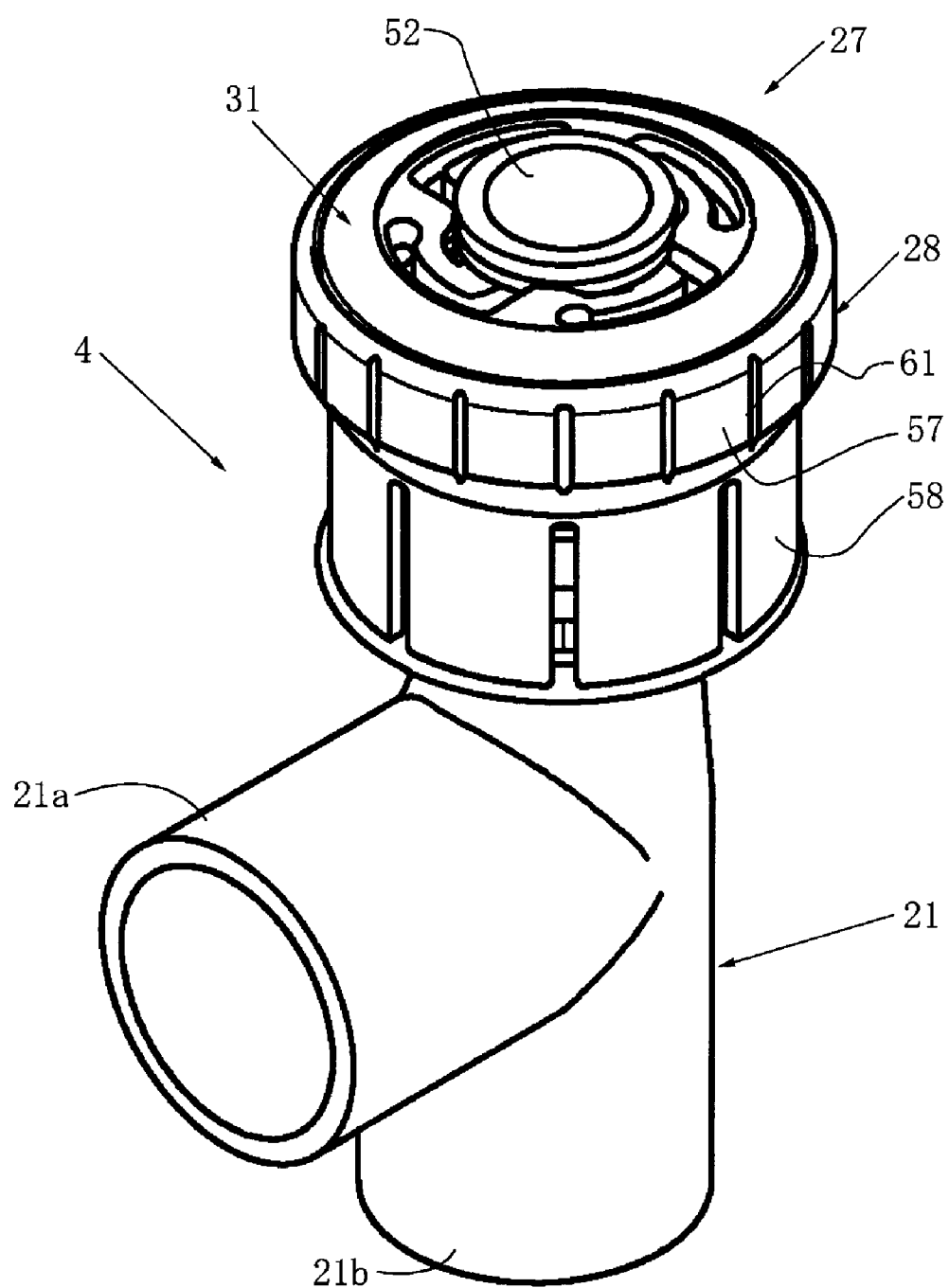
FIG. 1 is a perspective view showing an embodiment in which the present invention is applied to a pressure controller of a T-piece resuscitator.

An embodiment in which the present invention is applied to a pressure controller of a T-piece resuscitator will be explained below with reference to the accompanying drawings in the order of "1. Outline of Arrangement of Overall T-Piece Resuscitator", "2. Arrangement of Pressure Controller", "3. Procedures of Assembling Pressure Controller", "4. Operation of Pressure Controller", and "5. Method of Using T-Piece Resuscitator".

1. Outline of Arrangement of Overall T-Piece Resuscitator as Shown in FIG. 8, a T-Piece Resuscitator Includes:

(a) a resuscitator main body 1, (b) a gas source (not shown) that supplies an inspiratory gas to the resuscitator main body 1 through a gas supply tube 2, (c) a pressure controller 4 to which the resuscitator main body 1 supplies the inspiratory gas through a gas supply tube 3, and (d) a face mask 5 attached to the pressure controller 4.

Figure 11:
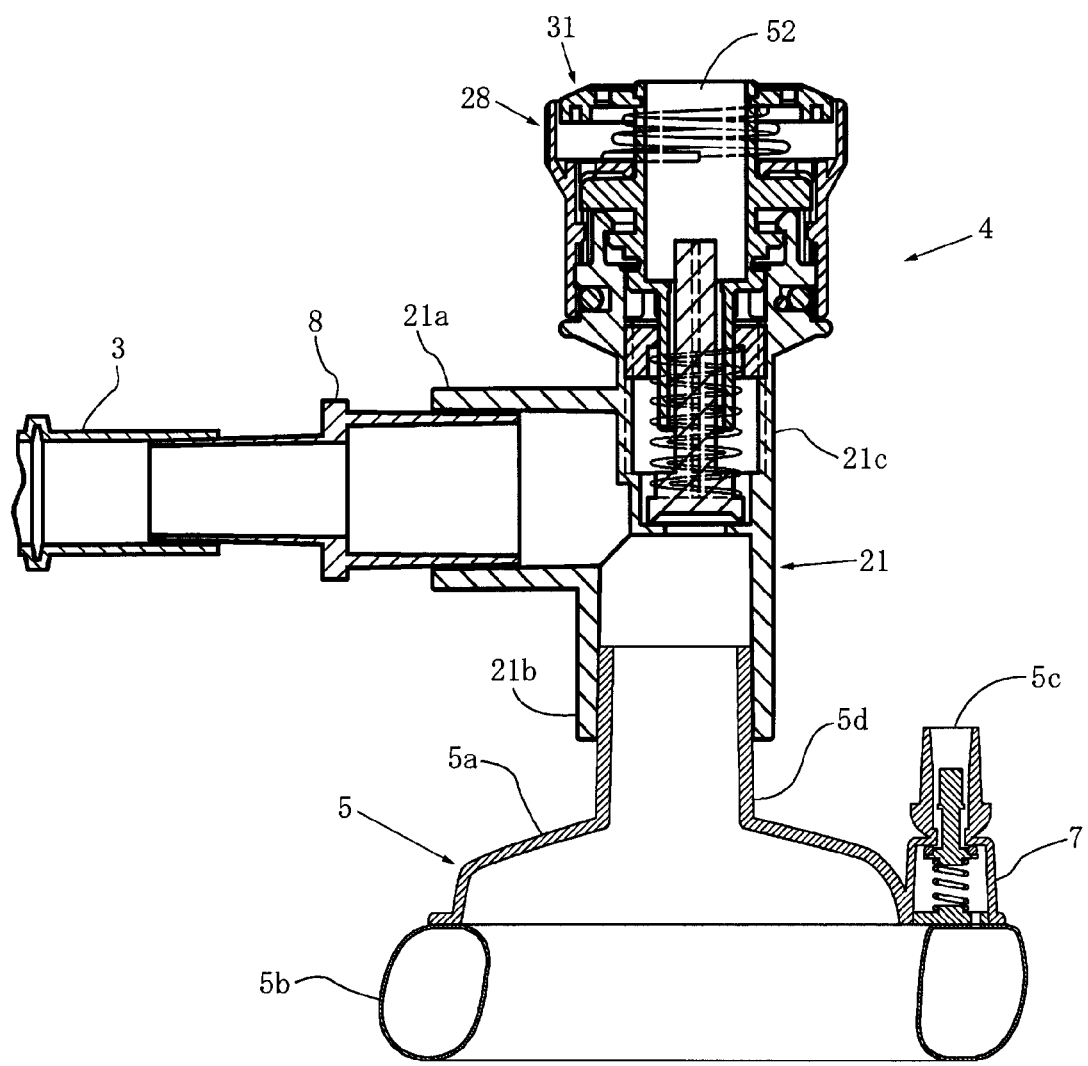
FIG. 11 is a longitudinal sectional view of the T-piece resuscitator shown in FIG. 10.

The pressure controller 4 is also called a patient T-piece. A ring-like air bag 5b having a shape like a small ring buoy is attached to the lower surface of a mask main body 5a of the face mask 5. The upper surface of the mask main body 5a has an air inlet/outlet pipe 5c to be used to let air in and let air out of the ring-like air bag 5b by using a syringe (in other words, a syringe having no needle attached; not shown) or the like. In addition, as shown in FIG. 11, a valve 7 to be opened or closed when letting air in or letting air out of the ring-like air bag 5b is formed between the air inlet/outlet pipe 5c and the upper surface of the ring-like air bag 5b. A connecting pipe 8 is attached to the distal end portion of the gas supply tube 3.

Figure 8:
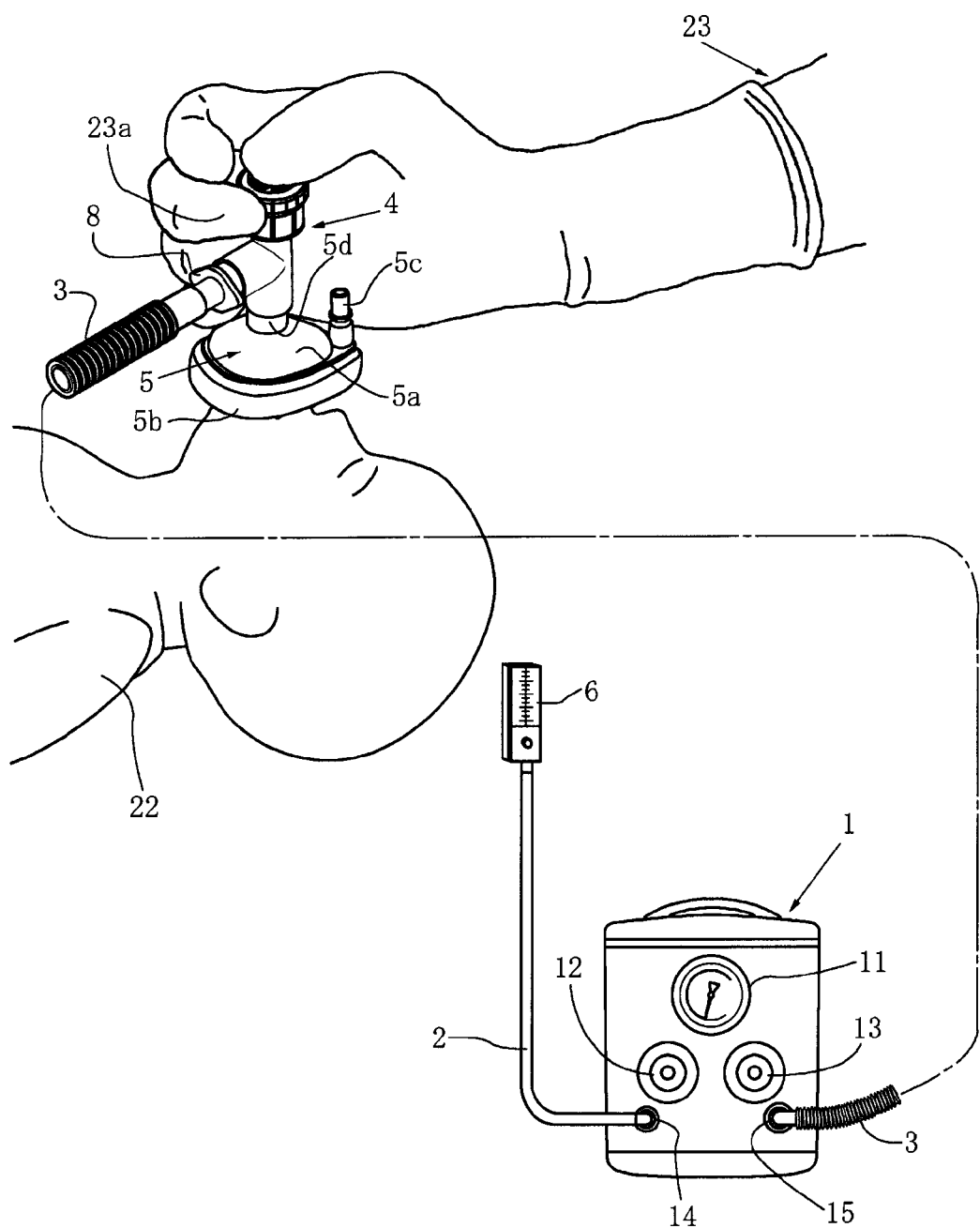
FIG. 8 is a schematic perspective view of a first form of the use state of the T-piece resuscitator incorporating the pressure controller shown in FIG. 1.

As shown in FIG. 8, a substantially tubular (e.g., a substantially cylindrical) inspiratory gas inlet 5d to be detachably connected to the pressure controller 4 is formed in a substantially central portion of the upper surface of the mask main body 5a. Note that the face mask 5 may also be a cannula such as a tracheal cannula or nasal cannula. Reference numeral 6 denotes a flowmeter of the gas source. The flowmeter 6 is used to control the flow rate of the inspiratory gas to be supplied from the gas source to the resuscitator device main body 1 through the gas supply tube 2. Note that in FIG. 8, the resuscitator main body 1 and its vicinity are reduced compared to other portions.

As shown in FIG. 8, the resuscitator main body 1 includes:

(e) a circuit pressure gauge 11 that displays the circuit pressure, (f) a peak release pressure control knob 12 to be used to control the peak release pressure, and (g) an inspiratory pressure control knob 13 to be used to control the inspiratory pressure.

The resuscitator main body 1 also has a gas supply hole 14 and gas discharge hole 15. The terminal end portion of the gas supply tube 2 is connected to the gas supply hole 14. The start end portion of the gas supply tube 3 is connected to the gas discharge hole 15.

2. Arrangement of Pressure Controller

Figure 9:
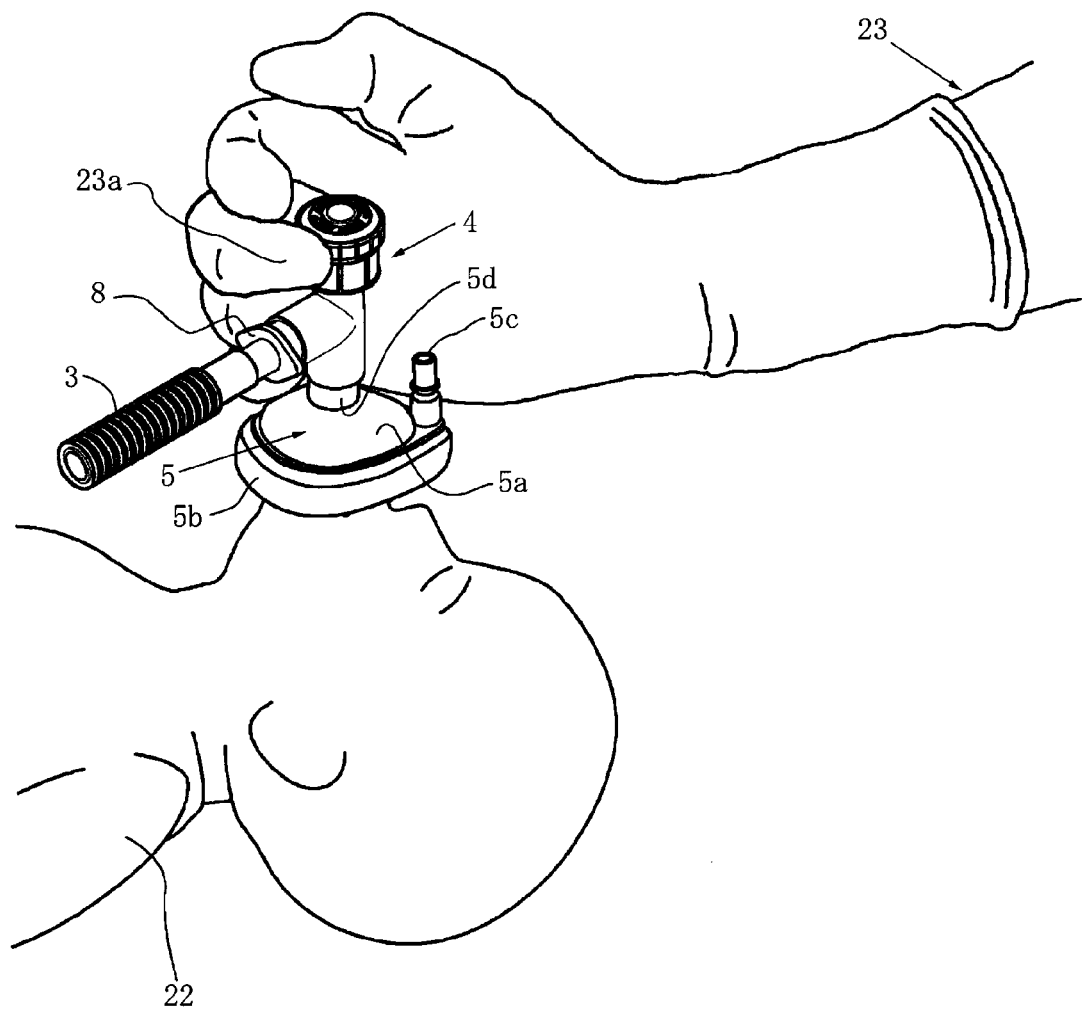
FIG. 9 is a schematic perspective view of a second farm of the use state of the T-piece resuscitator shown in FIG. 8, in which a resuscitator main body is not shown.
Figure 10:
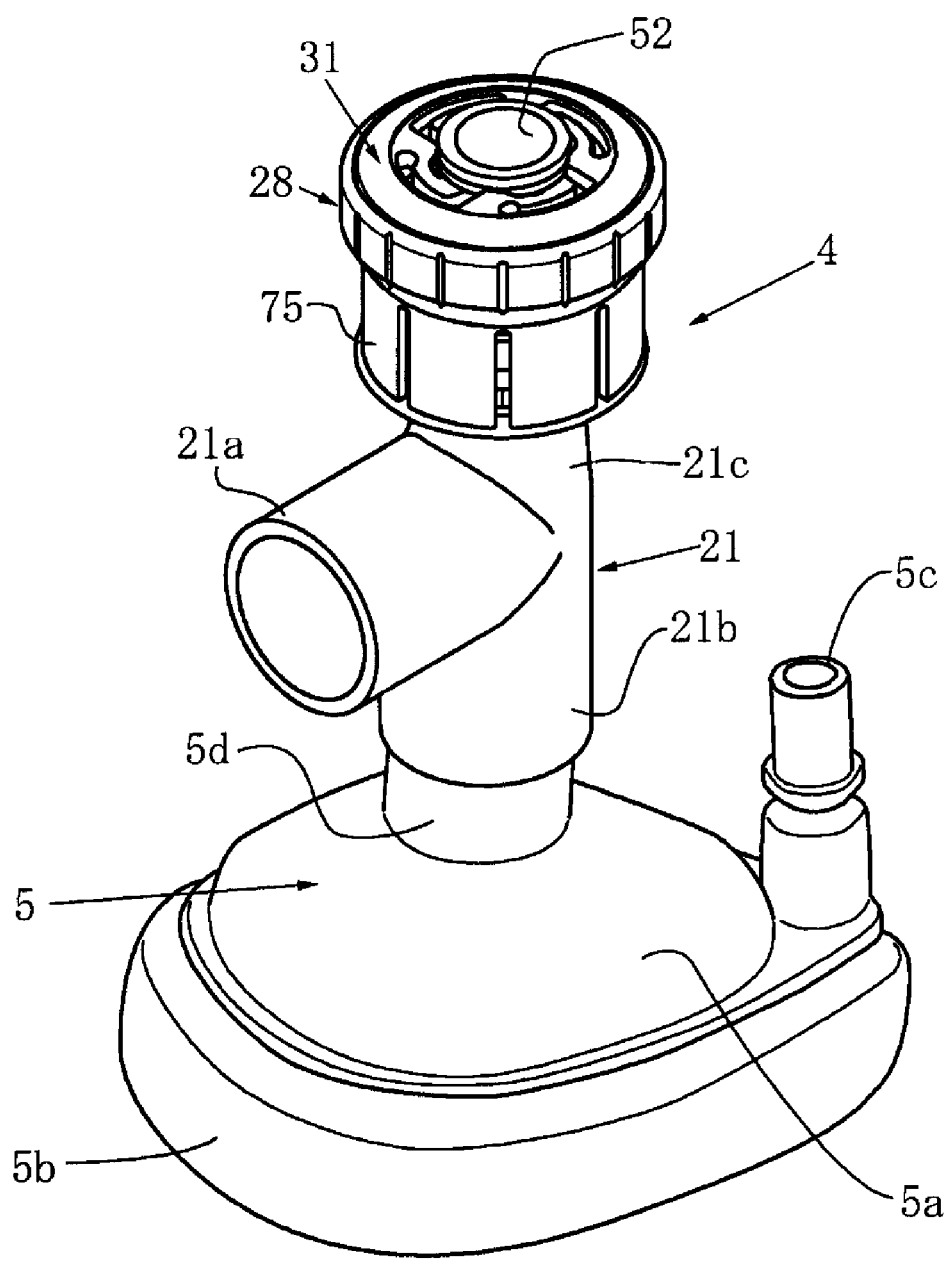
FIG. 10 is a perspective view when the T-piece resuscitator shown in FIG. 8 is in the first use state, in which the resuscitator main body is not shown.
Figure 12:
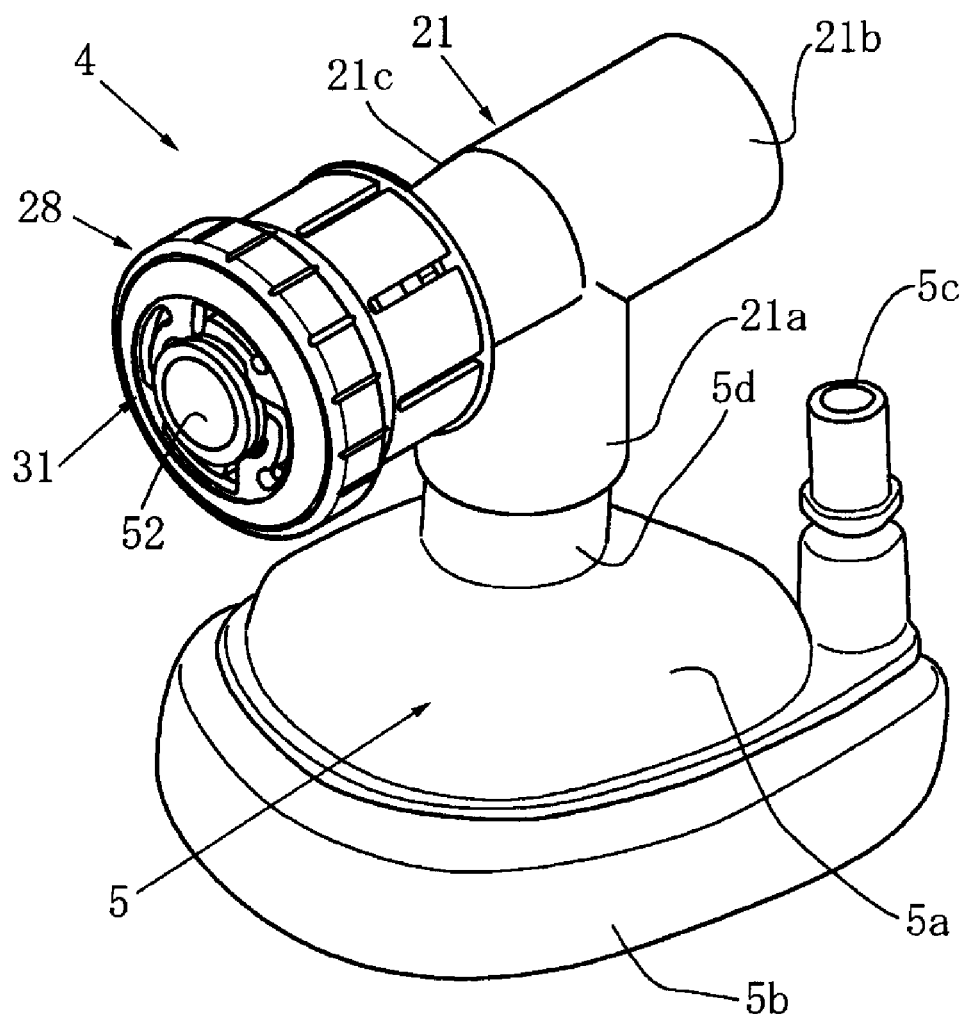
FIG. 12 is a perspective view similar to FIG. 8 when the T-piece resuscitator shown in FIG. 8 is in the second use state.
Figure 13:
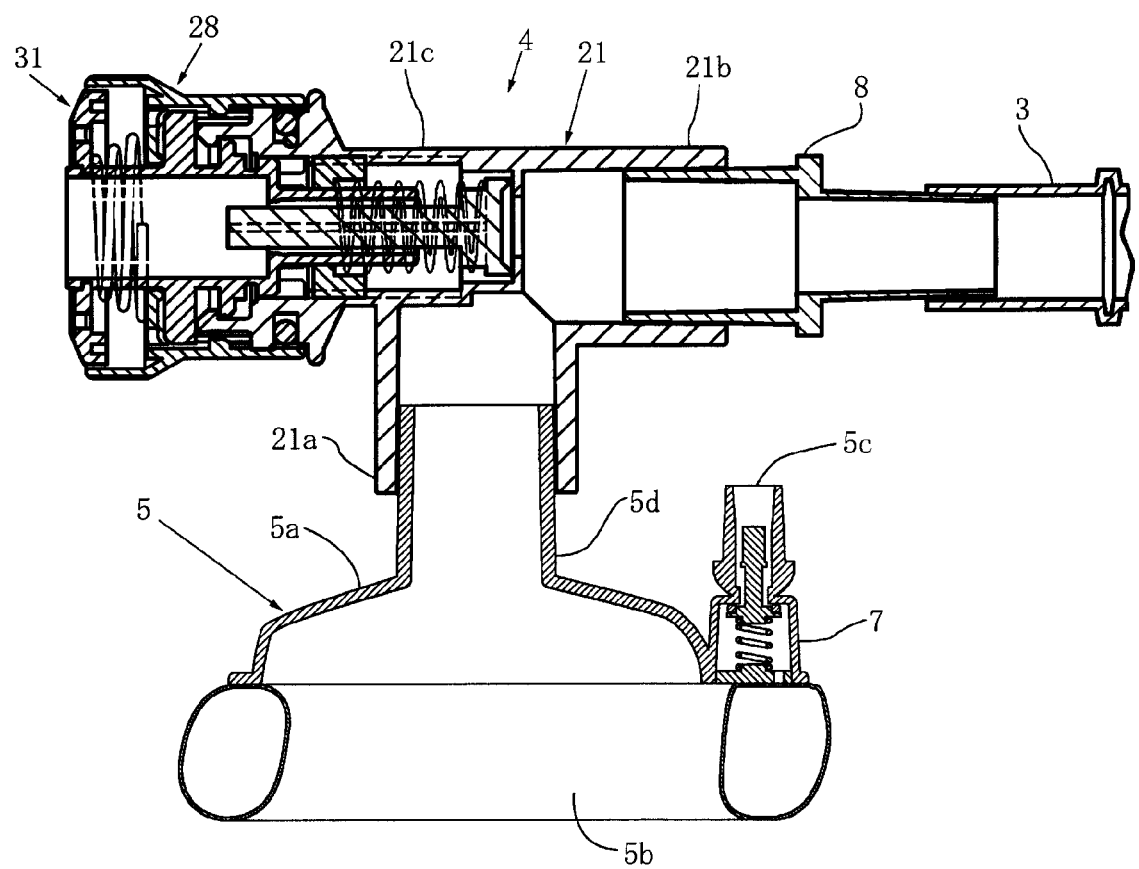
FIG. 13 is a longitudinal sectional view of the T-piece resuscitator shown in FIG. 12.
Figure 14:
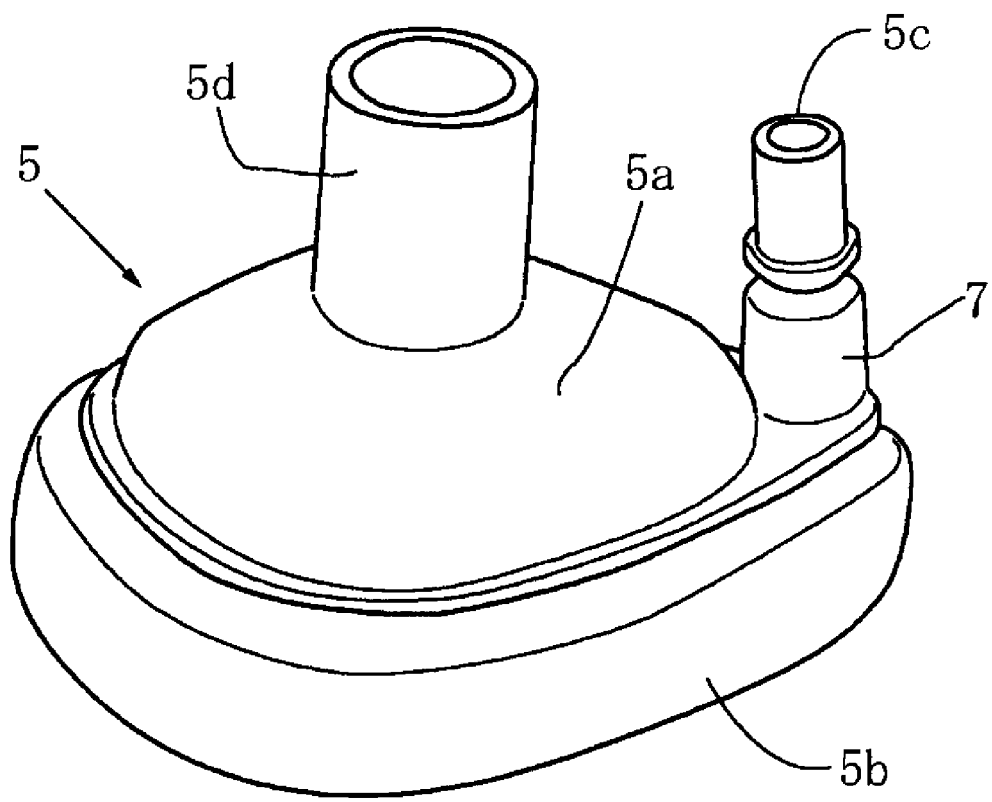
FIG. 14 is a perspective view of a face mask shown in FIG. 10.

As shown in FIGS. 1 to 4, the pressure controller 4 includes a substantially T-shaped branch pipe (in other words, a manifold as a housing mechanism) 21 having a branch pipe portion 21a as a first pipe joint or first vent hole. The gas supply tube 3 is connected to the branch pipe portion 21a as shown in FIGS. 8, 9 and 11, or the inspiratory gas inlet 5d of the face mask 5 shown in FIG. 14 is detachably attached to the branch pipe portion 21a. When the male-type gas supply tube 3 is connected to the female-type branch pipe portion 21a (in other words, in the first use state of the T-piece resuscitator), the branch pipe portion 21a forms an inspiratory gas supply hole as an inspiratory gas inlet. When the male-type inspiratory gas inlet 5d is attached to the female-type branch pipe portion 21a {in other words, in the second use state of the T-piece resuscitator), the branch pipe portion 21a forms a gas inlet/outlet portion for a patient 22 as an inspiratory gas outlet. Furthermore, in the first use state as shown in FIGS. 8, 9, 10 and 11, the inspiratory gas inlet 5d of the face mask 5 shown in FIG. 14 is detachably attached to another vent hole (the lower-half portion of the manifold 21 in the state shown in FIG. 3, i.e., a second pipe joint or second vent hole) 21b different from the branch pipe portion 21a of the manifold 21. In the second use state, the gas supply tube 3 is connected to the vent hole 21b as shown in FIGS. 12 and 13. In the first use state, the second pipe joint 21b forms a gas inlet/outlet portion for the patient 22. In the second use state, the second pipe joint 21b forms an inspiratory gas supply hole.

Figure 3:
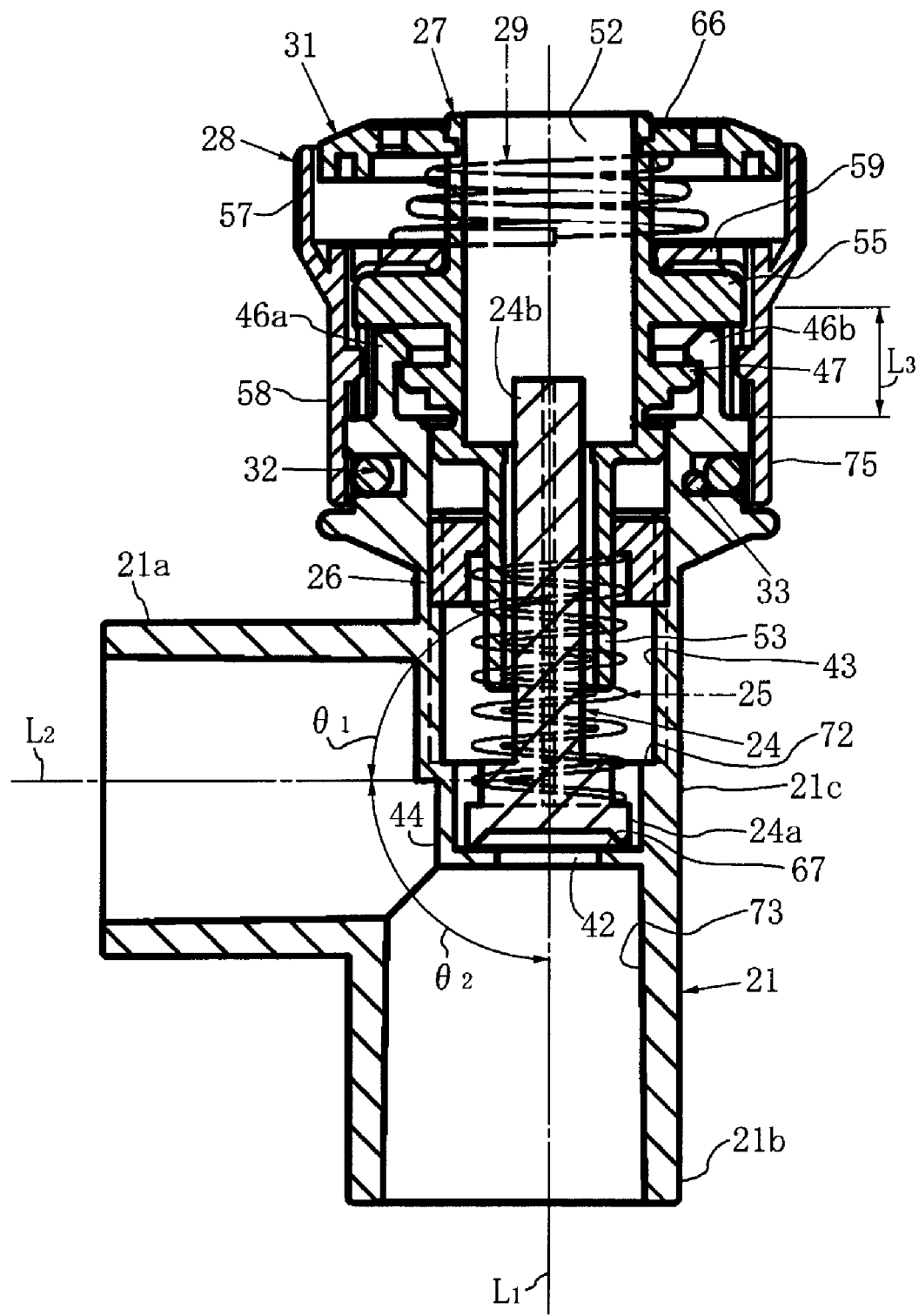
FIG. 3 is a longitudinal sectional view of the pressure controller shown in FIG. 1.

To make the T-piece resuscitator usable in both the first and second use states described above, conditions described in items (a) and (b) below are preferably met as shown in FIG. 3:

(a) the inner diameters of at least the distal end portions of the first pipe joint 21a and second pipe joint 21b are substantially the same, and (b) the outer diameter of at least the distal end portion of that portion of the connecting pipe 8 which is connected to the manifold 21, and the outer diameter of at least the distal end portion of the inspiratory gas inlet 5d are substantially the same.

Note that in the embodiment shown in the drawings, the inner diameter (in other words, the shape of the inner circumferential surface), the outer diameter (in other words, the shape of the outer circumferential surface) and the length of the first pipe joint 21a are respectively substantially the same as the inner diameter, outer diameter and length of the second pipe joint 21b as shown in FIG. 3.

As described above, the cylindrical inspiratory gas inlet 5d of the face mask 5 can selectively be fitted in and attached to the branch pipe portion 21a and second pipe joint 21b of the pressure controller 4. This enables an operator 23 to use the pressure controller 4 in two use states, i.e., a longitudinal use state (in other words, the above-mentioned first use state) shown in FIGS. 8, 9, 10 and 11, and a lateral use state (in other words, the second use state) shown in FIGS. 12 and 13. When this point is taken into consideration, an angle $\theta_1$ which a central line (in other words, an axis) $L_2$ of the manifold 21 makes with a central line $L_2$ of the branch pipe portion 21a is preferably about 90° as shown in FIG. 3. This similarly applies to an angle $\theta_2$ which the central line {in other words, the axis) $L_i$ of the lower-half portion 21b makes with the central line $L_2$ of the branch pipe portion 21a. More specifically, each of the angles $\theta_1$ and $\theta_2$ is about 90° in the embodiment shown in the drawings. From the viewpoint of practicality, each of the angles $\theta_1$ and $\theta_2$ is preferably 75° to 105°, more preferably, 80° to 100°, and most preferably, 85° to 95°.

Figure 2:
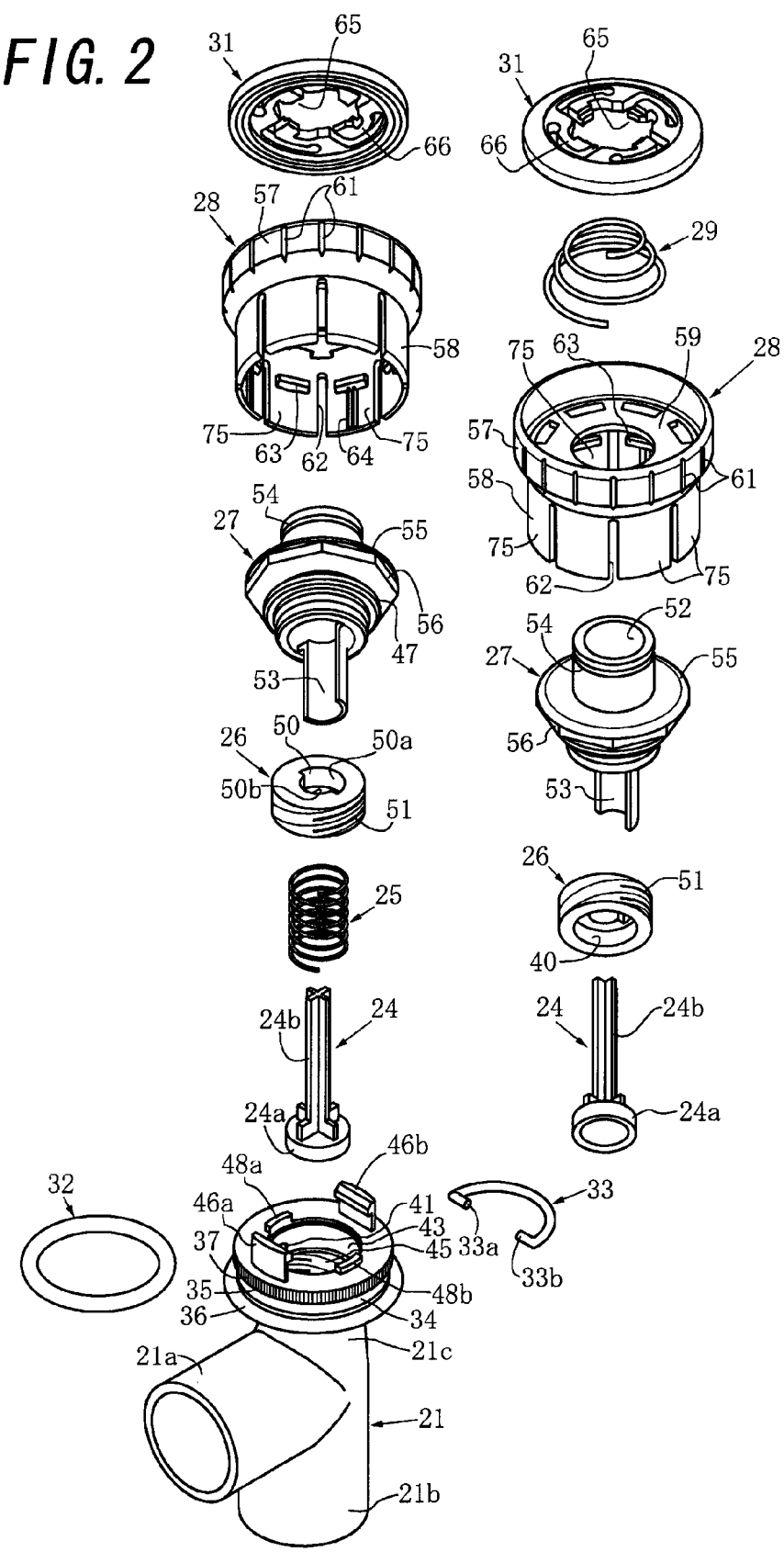
FIG. 2 is an exploded perspective view of the pressure controller shown in FIG. 1.

Parts described in items (c) to (j) below shown in FIG. 2 are attached to the manifold 21 in advance:

(c) a positive end expiratory pressure (PEEP) control valve 24, (d) a return coil spring 25 as an elastic biasing means, (e) a spring pressure control screw 26 as a second adjustment operating member or elevating adjustment operating member, (f) a pivotal adjustment operating member 27 as a first adjustment operating member, (g) an adjustment manipulating cap 28 as an adjustment manipulating member, (h) a repulsion conical coil spring (in other words, a trapezoidal coil spring) 29 as an elastic biasing means, (i) a top-surface member 31, and (j) an O-ring 32 and a substantially semi-circular stopper member 33.

Figure 7:
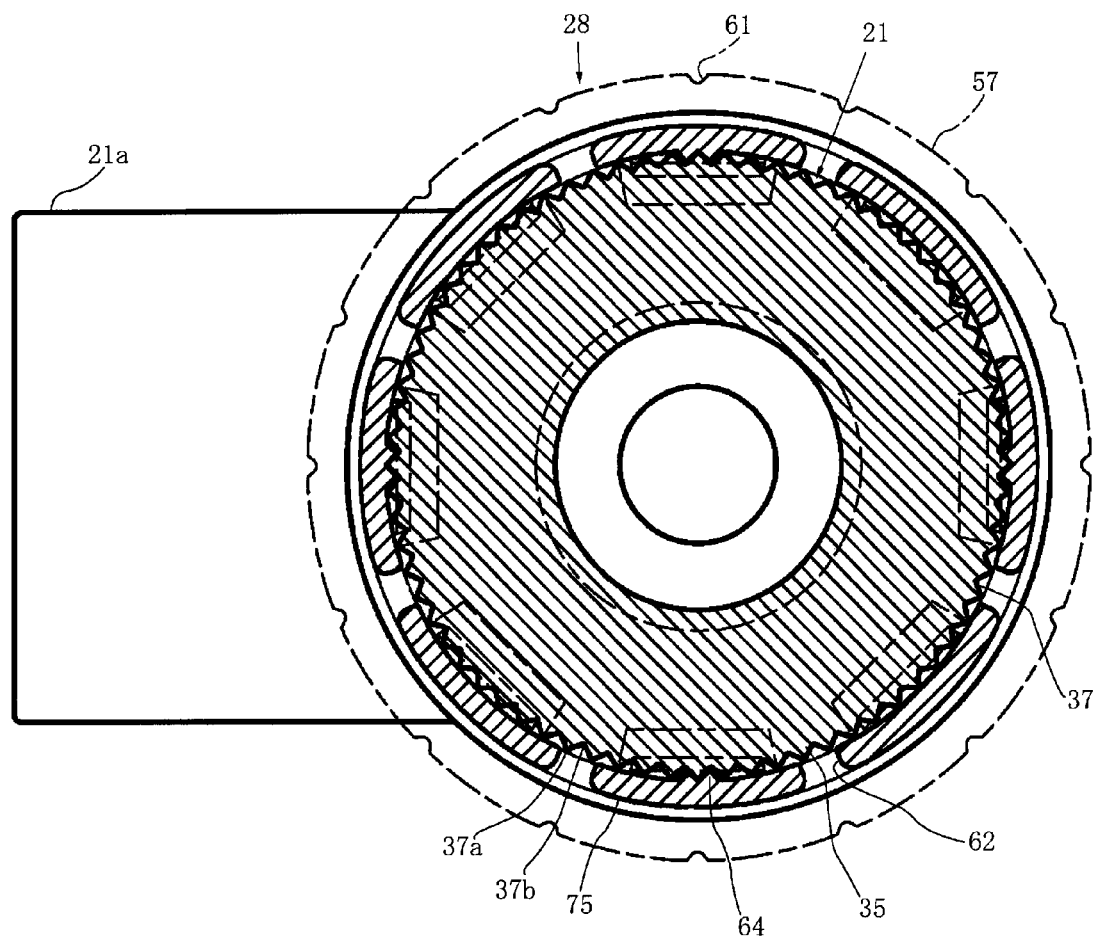
FIG. 7 is a sectional view taken along a line C-C in FIG. 4.
Figure 15A:
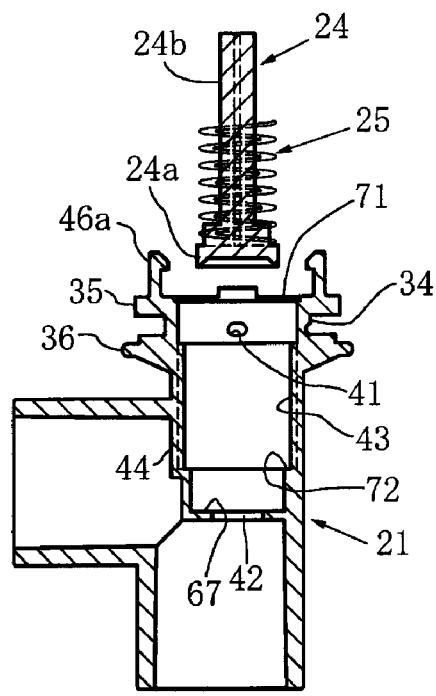
FIG. 15A is a longitudinal sectional view showing the first procedure of the procedures of assembling the pressure controller shown in FIG. 3 from the parts shown in FIG. 2.

Note that in FIG. 2, the PEEP control valve 24, spring pressure control screw 26, pivotal adjustment operating member 27, adjustment manipulating cap 28 and top-surface member 31 are viewed two ways, i.e., viewed obliquely from above and from below. As shown in FIGS. 3 and 15A, a substantially ring-like groove 34 for fitting the O-ring 32 in it is formed by a pair of upper and lower substantially ring-like projections 35 and 36 in an upper-half portion 21*c* of the manifold 21. Also, as shown in FIG. 2, a three-dimensional engaging portion 37 having a number of ridges vertically extending over substantially the entire length of the upper projection 35 is formed around substantially the entire circumferential surface of the projection 35. Note that as shown in FIGS. 2 and 7, the three-dimensional engaging portion 37 may also be formed by sequentially arranging projections 37*a* having a substantially triangular sectional shape (in other words, recesses 37*b* having a substantially triangular sectional shape) as the above-mentioned ridges adjacent to each other.

As shown in FIGS. 2 and 15A, a pair of attachment holes 41 facing each other at an angle of substantially 180° are formed in the substantially ring-like groove 34 of the manifold 21. Note that each of the pair of attachment holes 41 is a through hole. A pair of stopper end portions 33*a* and 33*b* facing each other as stopper means of a stopper member 33 are inserted into the through holes 41 in order to attach the stopper member 33 to the manifold 21. To this end, the pair of stopper end portions 33*a* and 33*b* protrude into an inner space 43 of the upper-half portion 21*c* of the manifold 21. Also, as shown in FIG. 3, an isolation wall 44 isolates the inner space 43 of the upper-half portion 21*c* of the manifold 21 from the branch pipe 21*a* and lower-half portion 21*b* of the manifold 21 (except for a vent hole 42}. A female screw 45 into which the spring pressure control screw 26 is to be screwed is formed on the inner circumferential surface of the lower portion of the upper-half portion 21*c*.

As shown in FIG. 2, a pair of locking pawls 46*a* and 46*b* facing each other at an angle of substantially 180° project from the upper surface of the manifold 21. The pair of locking pawls 46*a* and 46*b* is locked on the upper surface of a substantially ring-like portion 47 to be locked of the pivotal adjustment operating member 27. Also, a pair of positioning portions 48*a* and 48*b* facing each other at an angle of substantially 180° project from the upper surface of the manifold 21. Note that the pair of positioning portions 48*a* and 48*b* may make an angle of substantially 90° with the pair of locking pawls 46*a* and 46*b*. The lower surface of the portion 47 to be locked comes in contact with the upper surfaces of the pair of positioning portions 48*a* and 48*b*. Accordingly, the portion 47 to be locked is clamped between the pair of locking pawls 46*a* and 46*b* and the pair of positioning portions 48*a* and 48*b*, and fixed to the manifold 21 thereby.

Figure 15B:
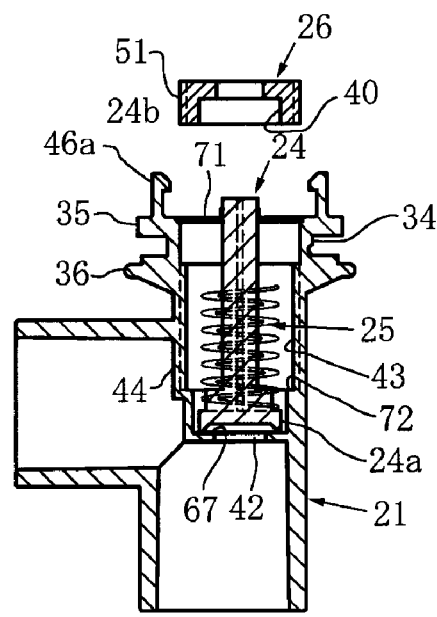
FIG. 15B is a longitudinal sectional view showing the second procedure of the assembling procedures.

As shown in FIG. 2, the PEEP control valve 24 includes a substantially cap-shaped valve body 24*a*, and a support shaft 24*b* integrally protruding from the upper surface of the valve body 24*a*. A male screw 51 is formed on the outer circumferential surface of the spring pressure control screw 26. Also, as shown in FIGS. 2 and 15B, a substantially columnar hole 40 having a substantially vertically extending axis is formed in the lower-half portion of the spring pressure control screw 26. Furthermore, a hole 50 that substantially vertically extends and communicates with the substantially columnar hole 40 is formed in the upper-half portion of the spring pressure control screw 26. One half of the hole 50 is formed by a substantially semi-circular, large-diameter hole 50*a* having substantially the same diameter as that of the hole 40. The other half of the hole 50 is formed by a substantially semi-circular, small-diameter hole 50*b*.

As shown in FIGS. 2 and 3, a central hole 52 that may have a substantially circular cross section is formed to substantially vertically extend through the upper-half portion of the pivotal adjustment operating member 27. The lower-half portion of the pivotal adjustment operating member 27 is formed by a substantially semi-tubular (e.g., a substantially semi-cylindrical) operating shaft 53. A substantially ring-like engaging groove 54 is formed in the outer circumferential surface in a region including the upper end and its vicinity of the pivotal adjustment operating member 27. Furthermore, a substantially disk-like, large-diameter portion 55 and an outer-circumference engaging portion 56 as a pivotal motion transmitting engaging portion formed adjacent to the lower surface of the large-diameter portion 55 are integrally formed in a middle portion in the vertical direction of the pivotal adjustment operating member 27. Note that the outer-circumference engaging portion 56 has a shape obtained by cutting the outer circumferential surface of the large-diameter portion 55 into a polygon (an octagon in the embodiment shown in the drawings), etc.

Figure 15C:
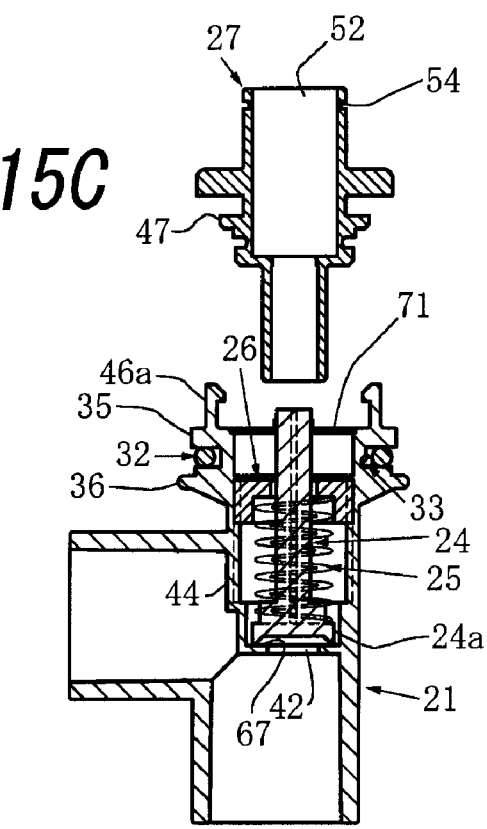
FIG. 15C is a longitudinal sectional view showing the third procedure of the assembling procedures.
Figure 15D:
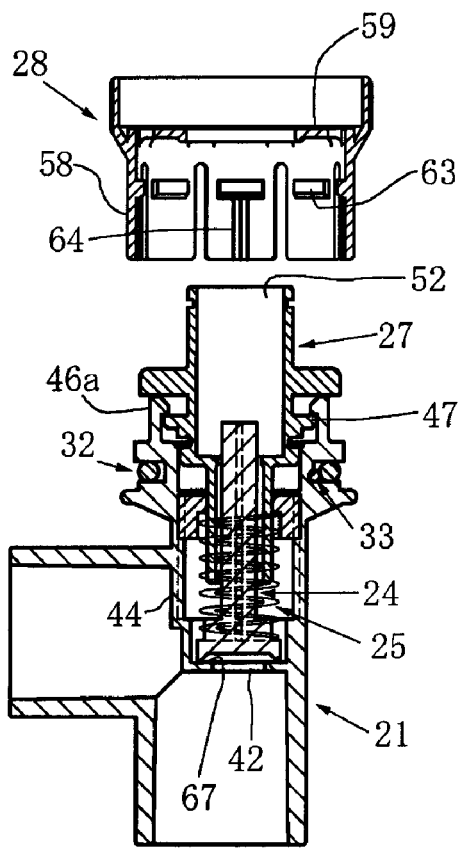
FIG. 15D is a longitudinal sectional view showing the fourth procedure of the assembling procedures.

As shown in FIGS. 2 and 15D, an upper-half portion 57 of the adjustment manipulating cap 28 is formed into a substantially tubular (e.g., a substantially cylindrical) shape having an open upper end. A lower-half portion 58 of the adjustment manipulating cap 28 is formed into a substantially cylindrical shape having a diameter slightly smaller than that of the upper-half portion 57. Between the upper-half portion 57 and lower-half portion 58, an intermediate plate 59 is formed integrally with the upper-half portion 57 and lower-half portion 58. In addition, in the outer circumferential surface of the upper-half portion 57, a number of grooves 61 are intermittently formed at substantially equal intervals so as to extend substantially vertically so that the operator 23 can easily grasp the upper-half portion 57 with a finger 23*a*. A plurality of {in the embodiment shown in the drawings, eight) slits 62 substantially vertically extending from the lower end to a region including the upper end and its vicinity are formed in the lower-half portion 58 of the adjustment manipulating cap 28.

Figure 5:
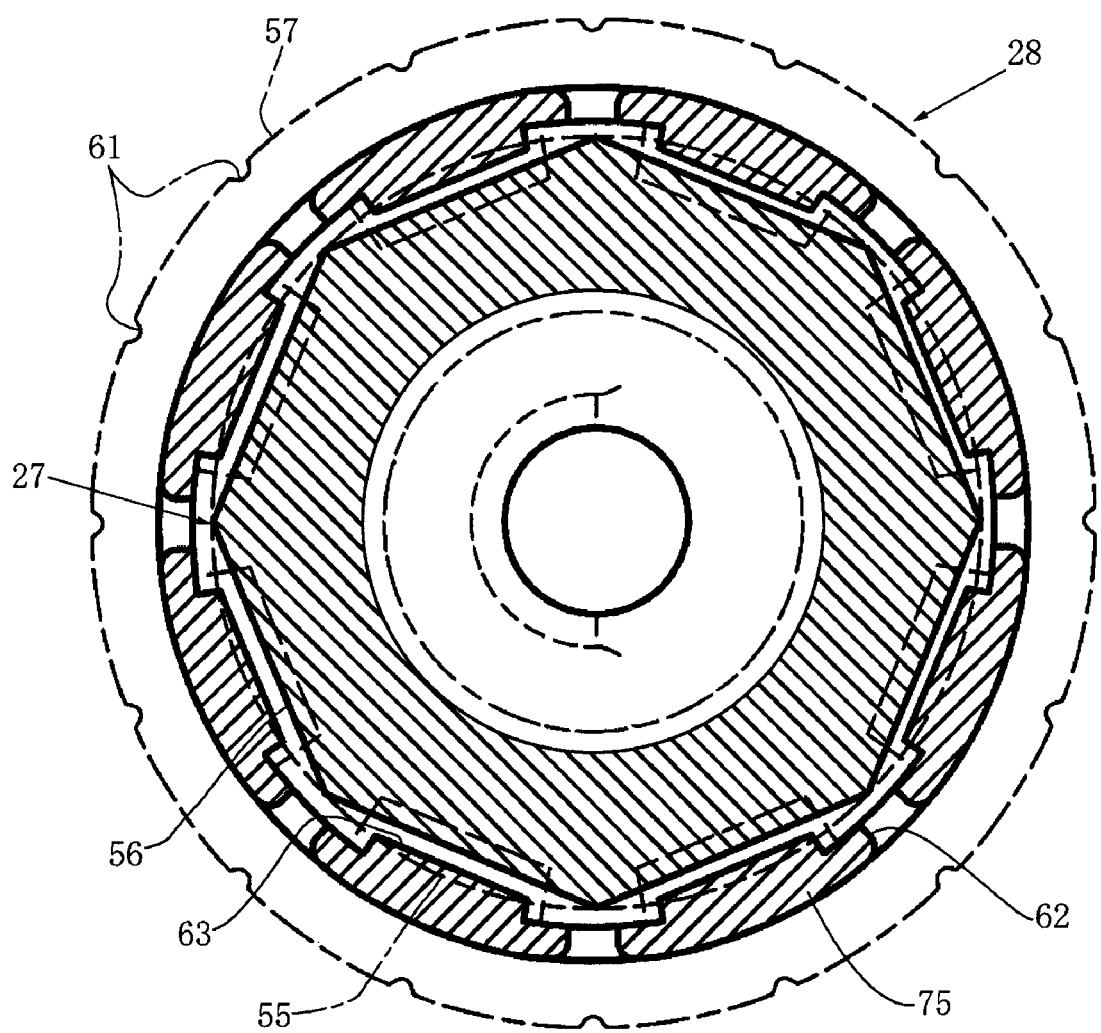
FIG. 5 is a sectional view taken along a line A-A in FIG. 4.

As shown in FIGS. 2, 5 and 15D, inner-circumference engaging portions 63 as pivotal motion transmitting engaging portions are integrally formed on the inner circumferential surface of the lower-half portion 58 of the adjustment manipulating cap 28, such that each inner-circumference engaging portion 63 is formed between a pair of slits 62 adjacent to each other. Accordingly, a plurality of in the embodiment shown in the drawings, eight) inner-circumference engaging portions 63 are formed on the inner circumferential surface of the lower-half portion 58. Each inner-circumference engaging portion 63 is formed as a substantially horizontal long bar so as to be able to face each flat surface of the outer-circumference engaging portion 56 of the pivotal adjustment operating member 27. Furthermore, a plurality of (in the embodiment shown in the drawings, two) engaging projections 64 as substantially vertically extending three-dimensional engaging portions are integrally formed on the inner circumferential surface of the lower-half portion 58 so as to be adjacent to the lower sides of a plurality of (in the embodiment shown in the drawings, four) inner-circumference engaging portions 63, e.g., every other inner-circumferential engaging portions 63.

As shown in FIGS. 2 and 15D, the plurality of slits 62 formed in the lower-half portion 58 of the adjustment manipulating cap 28 extend through the lower-half portion 58 of the adjustment manipulating cap 28 from the inner circumferential surface to the outer circumferential surface. Therefore, the slits 62 enable the circumferential portion of the lower-half portion 58 to readily elastically deform toward both the inner circumferential surface and outer circumferential surface with respect to the upper-half portion 57. When performing plastic molding of the adjustment manipulating cap 28, therefore, an inner metal mold is easily removed from the adjustment manipulating cap 28. Also, when putting the adjustment manipulating cap 28 on the pivotal adjustment operating member 27, the large-diameter portion 55 of the pivotal adjustment operating member 27 readily climbs over the inner-circumference engaging portions 63 of the adjustment manipulating cap 28 from the lower side to the upper side.

Figure 4:
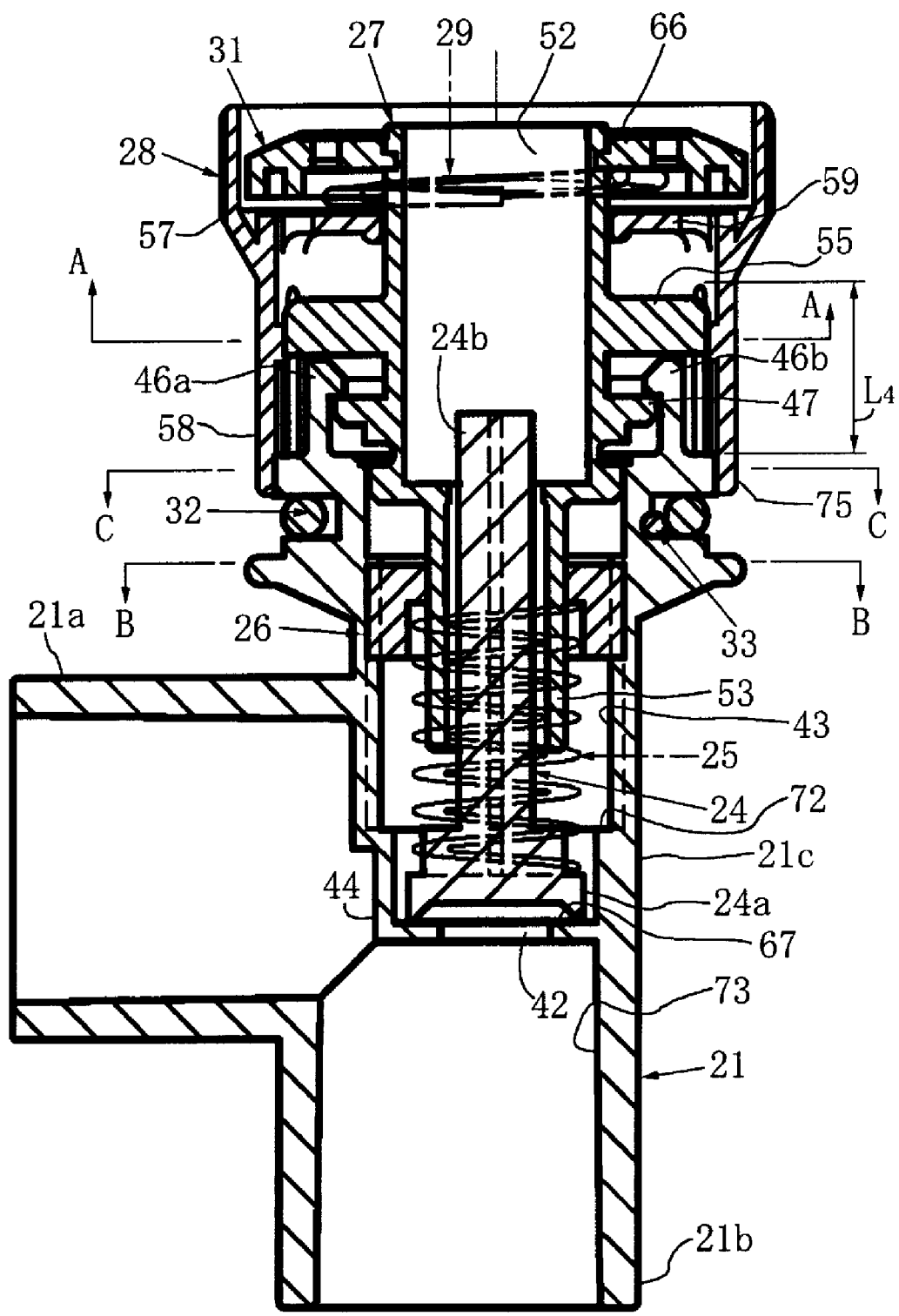
FIG. 4 is a longitudinal sectional view similar to FIG. 3 when setting the PEEP in the pressure controller shown in FIG. 1.

As shown in FIG. 4, the top-surface member 31 is formed into a substantially pot lid shape having an outer circumferential shape (in the embodiment shown in the drawings, a substantially disk shape) capable of accommodating the upper-half portion 57 of the adjustment manipulating cap 28. A central hole 65 substantially corresponding to the central hole 52 of the pivotal adjustment operating member 27 is formed in the top-surface member 31. Also, a plurality of (in the embodiment shown in the drawings, four) elastically deformable arms 66 are formed integrally with the top-surface member 31 so as to be adjacent to the central hole 65.

3. Procedures of Assembling Pressure Controller

Examples of the procedures of assembling the pressure controller 4 by attaching the parts {except for the manifold 21} shown in FIG. 2 to the manifold 21 as a housing mechanism will be explained below with reference to FIGS. 15A to 15F. The procedures are as described in items {a) to (g) below.

(a) First, as shown in FIG. 15A, the operating shaft 24b of the PEEP control valve 24 is relatively inserted into the return coil spring 25. Then, as shown in FIG. 15B, the valve body 24a of the PEEP control valve 24 is inserted into the inner space 43 of the upper-half portion 21c of the manifold 21 from an upper-end opening 71, and placed on a valve seat 67 formed by the outer-circumferential portion of the vent hole 42.

(b) Subsequently, as shown in FIGS. 15B and 15C, the spring pressure control screw 26 is inserted into the inner space 43 of the upper-half portion 21c of the manifold 21 from the upper-end opening 71. After that, the male screw 51 of the spring pressure control screw 26 is screwed into the female screw 45 of the manifold 21. In this state, the upper-end portion of the return coil spring 25 is relatively inserted into the columnar hole 40 of the spring pressure control screw 26. When the male screw 51 is kept screwed into the female screw 45, the spring pressure control screw 26 moves down as it rotates, but an upward position regulating step 72 formed in the inner space 43 of the upper-half portion 21c of the manifold 21 regulates the lowermost position of the spring pressure control screw 26.

(c) As shown in FIG. 15C, the stopper member 33 is fitted in the ring-like groove 34 of the manifold 21 such that the pair of stopper end portions 33a and 33b of the stopper member 33 extend through the pair of attachment holes 41 from the outer circumferential surface of the manifold 21, thereby attaching the stopper member 33 to the manifold 21. In this state, the distal end portions of the pair of stopper end portions 33a and 33b protrude into the inner space 43 of the upper-half portion 21c of the manifold 21. Accordingly, the end portions 33a and 33b regulate the uppermost position of the spring pressure control spring 26.

(d) As shown in FIG. 15C, the O-ring 32 is fitted in the ring-like groove 34 of the manifold 21. The O-ring 32 prevents a gas in the inner space 43 of the upper-half portion 21c of the manifold 21 from flowing outside the manifold 21 from the pair of attachment holes 41.

(e) As shown in FIGS. 15C and 15D, the pivotal adjustment operating member 27 is inserted into the inner space 43 of the upper-half portion 21c from the upper-end opening 71 of the manifold 21, and attached to the manifold 21 thereby. In this state, as described previously, the portion 47 to be locked of the adjustment operating member 27 is clamped between the pair of positioning portions 48a and 48b of the manifold 21 and the pair of locking pawls 46a and 46b, and fixed to the manifold 21 thereby. Also, the operating shaft 53 of the adjustment operating member 27 is inserted into the large-diameter hole 52a of the spring pressure control screw 26, and inserted into the coil spring 25 so as to surround the substantial half of the outer circumferential surface of the operating shaft 24b of the PEEP control valve 24.

Figure 15E:
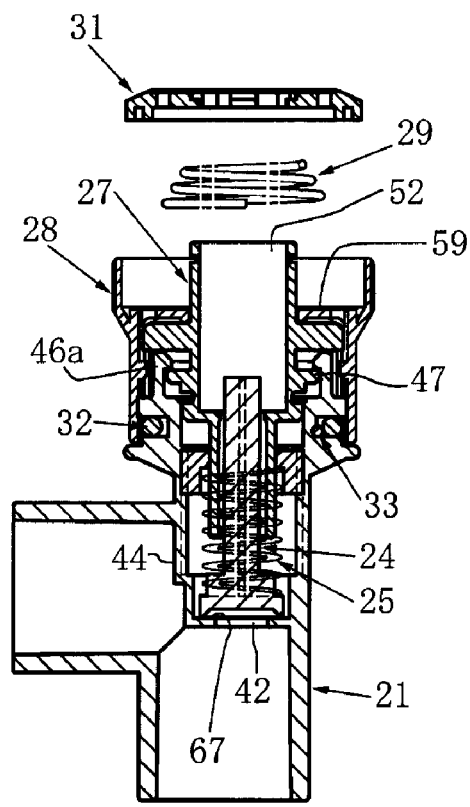
FIG. 15E is a longitudinal sectional view showing the fifth procedure of the assembling procedures.

(f) As shown in FIGS. 15D and 15E, the adjustment manipulating cap 28 is attached to the manifold 21 with the pivotal adjustment operating member 27 being interposed between them. When the adjustment manipulating cap 28 is put on the adjustment operating member 27, the plurality of inner-circumference engaging portions 63 formed on the inner circumferential surface of the adjustment manipulating cap 28 move downward through the large-diameter portion 55 of the adjustment operating member 27, and respectively face the plurality of outer-circumference engaging portions 56 of the adjustment operating member 27. This prevents the adjustment manipulating cap 28 from being removed from the adjustment operating member 27. In addition, the engaging projections 64 of the adjustment manipulating cap 28 three-dimensionally engage with the three-dimensional engaging portion 37 of the manifold 21 as shown in FIG. 7.

Figure 15F:
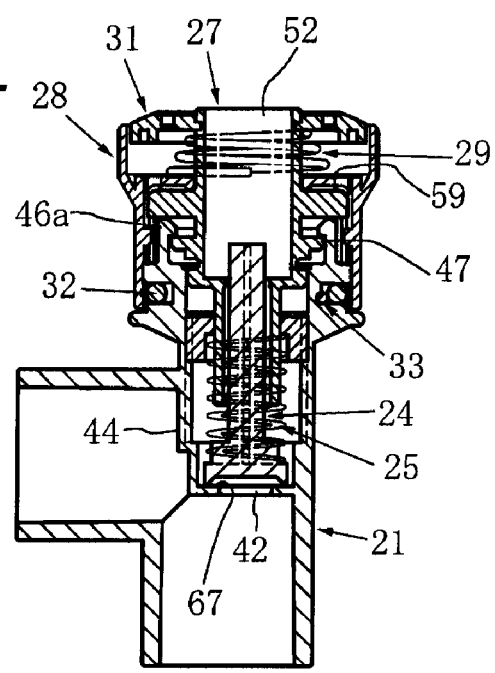
FIG. 15F is a longitudinal sectional view showing the sixth procedure of the assembling procedures.

(g) As shown in FIGS. 15E and 15F, the conical coil spring 29 and top-surface member 31 are sequentially accommodated in the upper-half portion 57 of the adjustment manipulating cap 28. In this state, the conical coil spring 2 9 is sandwiched between the intermediate plate 59 of the adjustment manipulating cap 2 8 and the top-surface member 31 around the outer circumferential surface of the pivotal adjustment operating member 27, and contracts to some extent. Also, the plurality of arms 66 of the top-surface member 31 once move away from the center of the central hole 65 in the top-surface member 31 to increase the size of the central hole 65, and then returns to the original position. Therefore, the distal end portions of the arms 66 engage with the engaging groove 54 of the pivotal adjustment operating member 27. This engagement prevents the removal of the top-surface member 31 from the adjustment operating member 27.

The pressure controller 4 shown in FIGS. 1, 3 and 4 can be assembled by performing the attaching operations as described in items (a) to (g) above. In the pressure controller 4 as described in item (f) above, the engaging projections 64 of the adjustment manipulating cap 28 three-dimensionally engage with the three-dimensional engaging portion 37 of the manifold 21 (see FIG. 7). Accordingly, when compared to a structure in which a smooth first engaging portion of the adjustment manipulating cap 28 engages with a smooth second engaging portion of the manifold 21 which has substantially the same shape as that of the first engaging portion in a satisfactory fitting state, the magnitude of the rotational torque when pivoting the adjustment manipulating cap 28 with respect to the manifold 21 has a sufficiently large value as described in "4. Operation of Pressure Controller" below.

4. Operation of Pressure Controller

The operation in the first use state (see FIGS. 8 to 11) of the pressure controller 4 will be explained below. Note that it is very obvious that substantially the same operation as that in the first use state is performed in the second use state (see FIGS. 12 and 13) of the pressure controller 4.

The gas supplied from the gas source through the gas supply tube 2, resuscitator main body 1, gas supply tube 3, and connecting pipe 8 shown in FIG. 8 is supplied into the manifold 21 from the first pipe joint (in other words, the inspiratory gas supply hole) 21a (in the second use state, the second pipe joint 21b) shown in FIG. 3. In this state, if the operator 23 such as a doctor closes the upper end of the central hole 52 of the pivotal adjustment operating member 27 with the finger 23a or the like, the gas does not flow outside from the central hole 52 whose upper end is closed with the finger 23a or the like even when the valve body 24a of the PEEP control valve 24 temporarily opens. Accordingly, the gas is supplied from the second pipe joint (in other words, the gas inlet/outlet portion for the patient 22) 21b to the patient 22 via the face mask 5. Also, when the operator 23 releases the finger 23a or the like from the upper end of the central hole 52, the gas supplied from the gas source into the manifold 21 as described above presses the lower surface of the valve body 24a of the PEEP control valve 24. In addition, the expiration from the patient 22 also presses the lower surface of the valve body 24a of the PEEP control valve 24 via the interior {in other words, a gas passage 73} of the gas inlet/outlet portion 21b of the manifold 21. This produces the possibility that the gas and expired air flow outside through the gap between the valve body 24a of the PEEP control valve 24 and the valve seat 67, the inner space 43, and the central hole (in other words, expiration exhaust hole} 52.

Figure 6:
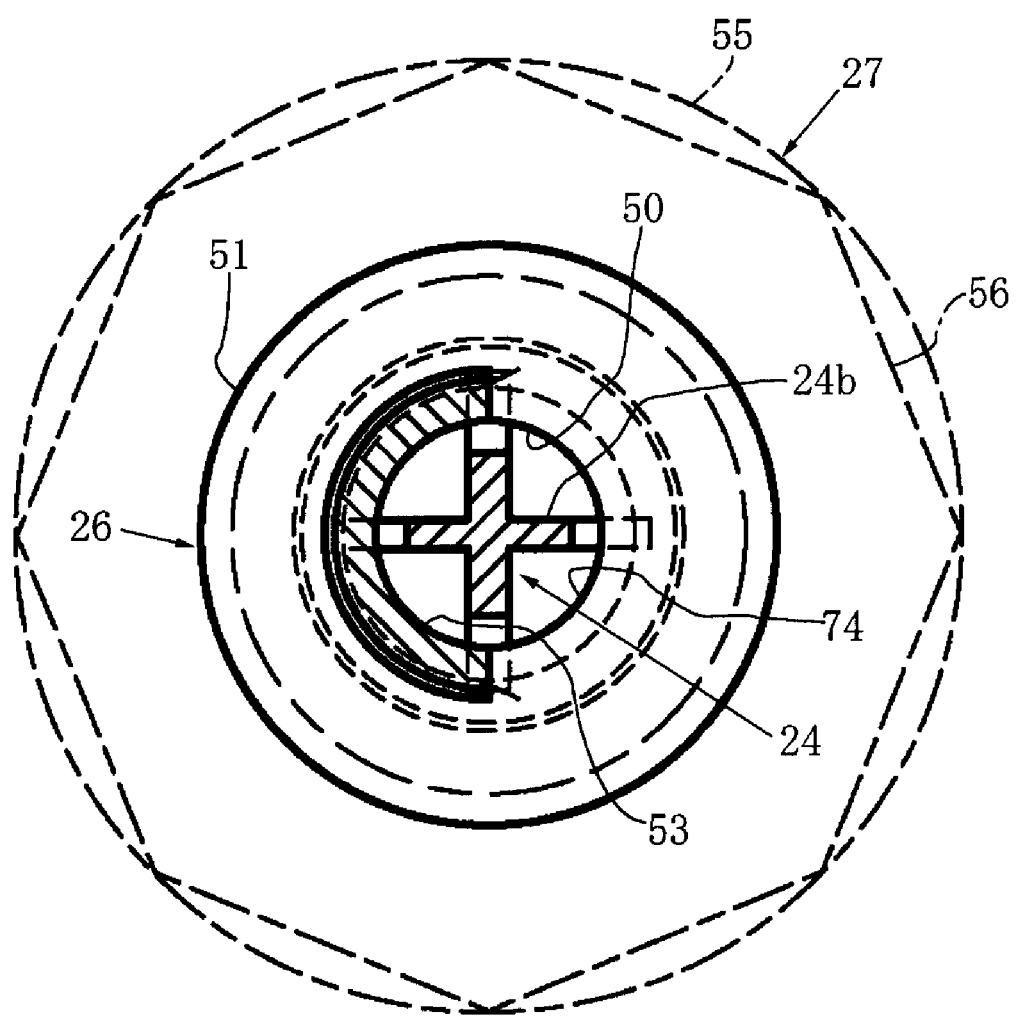
FIG. 6 is a sectional view taken along a line B-B in FIG. 4.

That is, as shown in FIG. 3, the coil spring 25 as an elastic biasing means elastically presses the valve body 24a of the PEEP control valve 24 against the valve seat 67. When the gas pressing force with which the gas from the gas source and the expired air from the patient 22 press the lower surface of the valve body 24a of the PEEP control valve 24 becomes larger than the elastic pressing force with which the coil spring 25 presses the upper surface of the valve body 24a of the PEEP control valve 24, the valve body 24a of the PEEP control valve 24 floats {in other words, separates upward) from the valve seat 67 by an amount corresponding to the difference. Consequently, the gas and expired air flow outside through:

(a) the gap between the valve body 24a of the PEEP control valve 24 and the valve seat 67 of the manifold 21, (b) a vent hole 74 (see FIG. 6) formed by the inner circumferential surface of the operating shaft 53 of the pivotal adjustment operating member 27 and the small-diameter hole 50b of the spring pressure control screw 26, and (c) the central hole 52 of the pivotal adjustment operating member 27.

The magnitude of the elastic pressing force with which the coil spring 25 presses the upper surface of the valve body 24a of the PEEP control valve 24 can be adjusted by manipulating the adjustment manipulating cap 28. This adjustment is performed as follows. First, the adjustment manipulating cap 28 shown in FIG. 3 is raised from the manifold 21, pivotal adjustment operating member 27, top-surface member 31 and the like against the elastic biasing force of the conical coil spring 29. As shown in FIGS. 4 and 5, this raise can be performed by the operator 23 with the fingers 23a until the inner-circumference engaging portions 63 of the adjustment manipulating cap 28 abut against the large-diameter portion 55 of the pivotal adjustment operating member 27. In this state, the conical coil spring 29 elastically deforms into a substantially flat shape as shown in FIG. 4. Also, as shown in FIGS. 4 and 5, the inner-circumference engaging portions 63 of the adjustment manipulating cap 28 become able to engage with the outer-circumference engaging portion 56 of the pivotal adjustment operating member 27. Therefore, by pivoting, clockwise or counterclockwise, the adjustment manipulating cap 28 which has been unable to engage with the adjustment operating member 27 in the pivoting direction, the pivotal adjustment operating member 27 (and in its turn the operating shaft 53} pivots together with the adjustment manipulating cap 28. As a consequence, the spring pressure control screw 26 also similarly pivots. Accordingly, the spring pressure control screw 26 having the male screw 51 screwed into the female screw 45 of the manifold 21 is further screw-tightened or screw-loosened (in other words, screwed upward or downward) with respect to the female screw 45, thereby rising or falling the screw 26 with respect to the manifold 21. Consequently, the coil spring 25 stretches as shown in FIG. 4, or contracts although not shown. Accordingly, the elastic pressing force with which the coil spring 25 presses the PEEP control valve 24 against the valve seat 67 decreases or increases.

Subsequently, when the operator 23 releases the fingers 23a or the like from the adjustment manipulating cap 28, the adjustment manipulating cap 28 returns to the position shown in FIG. 3 by the elastic biasing force of the conical coil spring 29. In this state, the adjustment manipulating cap 28 of course similarly returns even if it is pushed downward by the fingers 23a or the like. Note that when closing the upper end of the opening 52 with the finger 23a or the like as shown in FIG. 8 (in other words, in the state shown in FIG. 3}, even if the upper end portions of the adjustment operating member 27, top-surface member 31, adjustment manipulating cap 28 and the like are strongly pushed downward, the inner-circumference engaging portions 63 and outer-circumference engaging portion 56 do not unnecessarily engage with each other. This prevents the pivotal adjustment operating member 27 from pivoting by an operation error.

As shown in FIG. 7, the four longitudinal engaging projections 64 of the adjustment manipulating cap 28 always engage with the substantially ring-like, three-dimensional engaging portion 37 of the manifold 21 (in other words, in both the normal use state shown in FIG. 3 and the state shown in FIG. 4 in which the PEEP control valve 24 is adjusted). Therefore, the three-dimensional engaging portion 37 forms a first torque increasing means, and the engaging projections 64 form a second torque increasing means. Since the first and second torque increasing means 37 and 64 cooperate, the operator 23 has neither a sense of unease nor a sense of incompatibility in the normal use state shown in FIG. 3, unlike when the adjustment manipulating cap 28 easily and unexpectedly pivots with respect to the manifold 21. This enables the operator 23 to perform the normal use with a sense of security. Also, when adjusting the elastic pressing force with which the coil spring 25 presses the PEEP control valve 24 (see FIG. 4), the operator 23 has neither a sense of unease nor a sense of incompatibility and has no difficulty in finely adjusting the elastic pressing force, unlike when the adjustment manipulating cap 28 easily and unexpectedly pivots with respect to the manifold 21. Therefore, the operator 23 can perform adjustment and fine adjustment of the elastic pressing force with a sense of security.

In the normal use state shown in FIG. 3, a rotational torque required for the operator 23 to pivot the adjustment manipulating cap 28 with respect to the manifold 21 is about 10 cN*m in the embodiment shown in the drawings. From the viewpoint of practicality, this rotational torque is generally preferably 4 to 25 cN–m, more preferably, 5 to 20 cN–m, and most preferably, 7 to 15 cN–m.

On the other hand, in the adjustment state shown in FIG. 4, the above-mentioned rotational torque is about 4 cN–m in the embodiment shown in the drawings. Note that the rotational torque in the normal use state shown in FIG. 3 is about 2.5 times that in the adjustment state shown in FIG. 4 for the reason described below. That is, in the normal use state shown in FIG. 3, a portion having a length $L_3$ from the upper end of the slit 62 of the adjustment manipulating member 28 to a portion corresponding to the upper end of the three-dimensional engaging portion 37 of the manifold 21 functions as an effective spring portion of each of (a total of four) pressing leaf spring means 75. Therefore, the pressing leaf spring means 75 press the three-dimensional engaging portion 37. On the other hand, in the adjustment state shown in FIG. 4, a portion having a length $L_4$ from the upper end of the slit 62 of the adjustment manipulating member 28 to a portion corresponding to the upper end of the three-dimensional engaging portion 37 of the manifold 21 functions as an effective spring portion of each of (a total of four) pressing leaf spring means 75. Therefore, the pressing leaf spring means 75 press the three-dimensional engaging portion 37. Since the length $L_4$ is about 1.5 times the length $L_3$, the effective spring length $L_4$ of the four pressing leaf spring means 75 in the adjustment state shown in FIG. 4 is about 1.5 times the effective spring length $L_3$ of the four pressing leaf spring means 75 in the normal use state shown in FIG. 3. Accordingly, the pressing leaf spring means 75 having the effective spring length $L_4$ function as relatively soft leaf springs for the three-dimensional engaging portion 37. Also, the pressing leaf spring means 75 having the effective spring length $L_3$ function as relatively hard leaf springs for the three-dimensional engaging portion 37.

As described above, when the embodiment shown in the drawings is in the adjustment state shown in FIG. 4, the rotational torque required for the operator 23 to pivot the adjustment manipulating cap 28 with respect to the manifold 21 is about 4 cN–m. From the viewpoint of practicality, this rotational torque is generally preferably 1.5 to 10 cN–m, more preferably, 2 to 8 cN–m, and most preferably, 3 to 6 cN*m.

In the embodiment shown in the drawings, the ratio of the rotational torque in the normal use state shown in FIG. 3 to that in the adjustment state shown in FIG. 4 is about 2.5. From the viewpoint of practicality, this ratio is generally preferably 1.2 to 5, more preferably, 1.6 to 4, and most preferably, 2 to 3.

The rotational torque in the normal use state shown in FIG. 3 is relatively high in order to allow the operator to readily notice that the operation of pivoting the adjustment manipulating cap 28 in the normal use state shown in FIG. 3 is an operation error, and to prevent damage inflicted to the adjustment manipulating cap 28, adjustment operating member 27 and the like when the adjustment manipulating cap 28 does not pivot even if a large force is applied. Also, the rotational torque in the adjustment state shown in FIG. 4 is relatively low because if this rotational torque is too high, it becomes difficult to perform adjustment and fine adjustment by the pivoting operation of the adjustment manipulating cap 28.

5. Method of Using T-Piece Resuscitator

An example of a method of using the T-piece resuscitator shown in FIGS. 1 to 14 (in the first use state (see FIGS. 8 to 11) of the pressure controller 4) will be explained below. This method is as described in items (a) to (i) below. Note that it is very obvious that even in the second use state {see FIGS. 12 and 13) of the pressure controller 4, the T-piece resuscitator can be used by substantially the same method as in the first use state described above.

(a) First, a test lung (not shown) is attached to the second pipe joint 21b forming the gas inlet/outlet portion for the patient 22. This test lung can be an inflatable balloon.

(b) Then, the gas supply tube 2 shown in FIG. 8 is connected to the resuscitator main body 1.

(c) Subsequently, the flowmeter 6 shown in FIG. 8 is adjusted in order to adjust the amount of gas flowing into the T-piece resuscitator from the above-mentioned gas source.

(d) As shown in FIG. 8, while the upper-end opening of the central hole 62 in the pivotal adjustment operating member 27, which is open in a region including the top surface and its vicinity of the top-surface member 31, is blocked (i.e., closed) with the finger (in the embodiment shown in the drawings, the thumb) 23a of the operator 23 such as a doctor, the peak circuit pressure is set by setting the peak release pressure control knob 12 at a selected value.

(e) After that, as shown in FIG. 8, while the upper-end opening of the central hole 52 of the pivotal adjustment operating member 27 is closed with the finger 23a, the peak inspiratory pressure (in other words, PIP) is set by setting the inspiratory pressure control knob 13 at the peak inspiratory pressure.

(f) Then, the finger 23a is released from the upper-end opening of the central hole 52 in the pivotal adjustment operating member 27, and the adjustment manipulating cap 28 in the state shown in FIG. 3 is raised from the manifold 21 (and in its turn the pivotal adjustment operating member 27). This raise engages the inner-circumference engaging portions 63 of the adjustment manipulating cap 28 with the outer-circumference engaging portion 56 of the pivotal adjustment operating member 27. In this step, the adjustment manipulating cap 28 need only be raised until it cannot be raised any more because the inner-circumference engaging portions 63 of the adjustment manipulating cap 28 abut against the head 55 of the pivotal adjustment operating member 27. Subsequently, the adjustment manipulating cap 28 is pivoted clockwise or counterclockwise as needed with the fingers 23a. Since this pivotal motion makes it possible to pivot the pivotal adjustment operating member 27 clockwise or counterclockwise as needed, the PEEP (i.e., the positive end expiratory pressure) can be set at a desired value.

(g) The test lung described above is detached from the gas inlet/outlet portion (in other words, the second pipe joint) 21b for the patient 22, and the face mask 5 is attached to the gas inlet/outlet portion 21b. The face mask 5 is then put on the mouth of the patient 22 as shown in FIGS. 8 and 9.

(h) As shown in FIG. 8, the number of times of respiration of the patient 22 is controlled by intermittently blocking the upper-end opening of the central hole 52 in the pivotal adjustment operating member 27 with the finger 23a.

(i) When changing the peak inspiratory pressure described in item (e) above, the inspiratory pressure control knob 13 shown in FIG. 8 must be controlled again. This can be done while ventilation is performed on the patient 22, and the above-mentioned test lung need not be reattached.

Having described a specific preferred embodiment of this invention with reference to the accompanying drawings, it is to be understood that the invention is not limited to that precise embodiment, and that various changes and modifications may be effected therein by one skilled in the art without departing from the scope or spirit of the invention as defined in the appended claims.

For example, although the present invention is applied to the pressure controller 4 of the T-piece resuscitator device in the embodiment described above, the present invention is also applicable to a pressure controller of a resuscitator other than the T-piece resuscitator or a pressure controller of another artificial respirator.

Also, in the above-mentioned embodiment, the four longitudinal engaging projections 64 as the second three-dimensional engaging portions of the adjustment manipulating cap 28 engage with the substantially ring-like, three-dimensional engaging portion 37 as the first three-dimensional engaging portion of the manifold 21 even in the normal use state shown in FIG. 3. Therefore, the adjustment manipulating cap 28 does not easily and unexpectedly pivot with respect to the manifold 21. However, it is also possible to prevent the first three-dimensional engaging portions 64 from engaging with the second three-dimensional engaging portion 37 as needed in the normal use state shown in FIG. 3. In this case, the adjustment manipulating cap 28 lightly idles with respect to the manifold 21 in the normal use state shown in FIG. 3.

In the above embodiment, the adjustment operating member is made up of the spring pressure control screw 26 and pivotal adjustment operating member 27. However, the adjustment operating member may also be a single member obtained by integrally connecting the spring pressure control screw 26 and pivotal adjustment operating member 27. In this case, the inner-circumference engaging portions 63 of the adjustment manipulating cap 28 and/or the outer-circumference engaging portion 56 of the pivotal adjustment operating member 27 need only be relatively lengthened in the axial direction.

In the above embodiment, the adjustment manipulating member 28 is formed into a substantially cap shape. However, the adjustment manipulating member 28 may also be formed into a substantially disk shape or plate shape. In this case, the substantially plate-like adjustment manipulating member 28 need only be pivotal and slidable in the axial direction with respect to the cylinder shaft of the pivotal adjustment operating member 27.

In the above embodiment, the coil spring 25 is used as an elastic biasing means. However, the elastic biasing means may also be a leaf spring having a substantially wave shape such as a substantially S-shape, or a substantially columnar elastic member made of an elastic material such as rubber. In this case, the two end portions of the leaf spring or elastic column can be supported by the spring-receiving recess or spring-receiving upper surface of the control valve 24 and the spring-receiving recess of the spring pressure control screw 26, respectively. One end portion of the elastic column may also be used as the control valve.

In the above embodiment, the second adjustment operating member (in other words, spring pressure control screw) 26 is screwed by the female screw (in other words, the feed screw) 45 formed on the inner circumferential surface of the upper-half portion 21c of the manifold 21. However, the second adjustment operating member 26 may also be fed by a cam groove formed in the inner circumferential surface of the upper-half portion 21c of the manifold 21 and a cam follower formed on the second adjustment operating member 26.

In the above embodiment, the projections 64 are formed as the second torque increasing means or second three-dimensional engaging portions on the adjustment manipulating cap 28. However, the second torque increasing means or second three-dimensional engaging portions may also be recesses.

Furthermore, in the above embodiment, the first three-dimensional engaging portion 3 7 as the first torque increasing means is formed by a number of ridges formed on substantially the entire circumferential surface of the ring-like projection 35 of the upper-half portion 21c of the manifold 21. In addition, the second three-dimensional engaging portions 64 as the second torque increasing means are formed by a plurality of, e.g., four engaging projections 64 intermittently formed on the inner circumferential surface of the lower-half portion 58 of the adjustment manipulating cap 28. However, one or both of the first and second torque increasing means may also be surfaces on which a large number of regular or irregular bump-like projections are integrally formed. One or both of the first and second torque increasing means may also be simple rough surfaces having a relatively large friction coefficient. These rough surfaces may also be made of rubber. The outer circumferential surface of the ring-like projection 35 of the upper-half portion 21c of the manifold 21 may also be pressed into the inner circumferential surface of the lower-half portion 58 of the adjustment manipulating cap 28 by making the diameter of the inner circumferential surface of the lower-half portion 58 smaller than that of the outer circumferential surface of the ring-like projection 35 to some extent. In this case, one or both of the first and second torque increasing means need not be three-dimensional engaging portions.

The invention claimed is:

1. A pressure controller for use in an artificial respirator for supplying a gas to a patient requiring respiration assistance, comprising:

a housing mechanism which has a first vent hole, a second vent hole and a third vent hole, and in which one of the first vent hole and the second vent hole is configured to be used as an inlet of an inspiratory gas and the other vent hole is configured to be used as an outlet of the inspiratory gas;

a control valve placed in said housing mechanism to face a gas passage between the first vent hole and the second vent hole;

elastic biasing means for elastically biasing said control valve against a valve seat formed in said housing mechanism;

an adjustment operating member to be operated to adjust an elastic biasing force of said elastic biasing means; and an adjustment manipulating member to be pivoted to operate said adjustment operating member, wherein said control valve closes the third vent hole when a gas pressure in the gas passage is lower than a predetermined level, and said control valve opens the third vent hole such that a gas in the gas passage flows through the third vent hole when the gas pressure in the gas passage is higher than a predetermined level, wherein said adjustment operating member does not operate even when said adjustment manipulating member pivots by a pivoting operation of said adjustment manipulating member in a first state in which said adjustment manipulating member is not drawn outwardly against said adjustment operating member, and said adjustment operating member operates to adjust the elastic biasing force of said elastic biasing means when said adjustment manipulating member pivots by the pivoting operation of said adjustment manipulating member in a second state in which said adjustment manipulating member is drawn outwardly against said adjustment operating member.

2. A controller according to claim 1,
wherein a rotational torque required to pivot said adjustment manipulating member in the first state is 4 to 25 cN–m.

3. A controller according to claim 1,
wherein a rotational torque required to pivot said adjustment manipulating member in the first state is 5 to 20 cN–m.

4. A controller according to claim 1,
wherein a rotational torque required to pivot said adjustment manipulating member in the first state is 7 to 15 cN–m.

5. A controller according to claim 1,
wherein a rotational torque required to pivot said adjustment manipulating member in the second state is 1.5 to 10 cN–m.

6. A controller according to claim 1,
wherein a rotational torque required to pivot said adjustment manipulating member in the second state is 2 to 8 cN–m.

7. A controller according to claim 1,
wherein a rotational torque required to pivot said adjustment manipulating member in the second state is 3 to 6 cN*m.

8. A controller according to claim 1,
wherein a ratio of the rotational torque required to pivot said adjustment manipulating member in the first state to the rotational torque required to pivot said adjustment manipulating member in the second state is 1.2 to 5.

9. A controller according to claim 1,
wherein a ratio of the rotational torque required to pivot said adjustment manipulating member in the first state to the rotational torque required to pivot said adjustment manipulating member in the second state is 1.6 to 4.

10. A controller according to claim 1,
wherein a ratio of the rotational torque required to pivot said adjustment manipulating member in the first state to the rotational torque required to pivot said adjustment manipulating member in the second state is 2 to 3.

11. A controller according to claim 1,
wherein a first three-dimensional engaging portion is formed on a side of said housing mechanism, and a second three-dimensional engaging portion configured to engage with said first three-dimensional engaging portion is formed on a side of said adjustment manipulating member, and
engagement of said first three-dimensional engaging portion and said second three-dimensional engaging portion in the first state increases the rotational torque required to pivot said adjustment manipulating member.

12. A controller according to claim 11,
wherein engagement of said first three-dimensional engaging portion and said second three-dimensional engaging portion in the second state increases the rotational torque required to pivot said adjustment manipulating member.

13. A controller according to claim 11,
wherein said first three-dimensional engaging portion is a three-dimensional engaging portion formed into a substantially ring shape on an outer circumferential surface of said housing mechanism, and
said second three-dimensional engaging portion comprises a plurality of three-dimensional engaging portions intermittently formed on an inner circumferential surface of said adjustment manipulating member.

14. A controller according to claim 1,
wherein said controller comprises a top-surface member attached to a side of said housing mechanism such that said top-surface member does not move forward and backward in the direction in which said adjustment manipulating member is pulled out; and
a conical coil spring interposed between said top-surface member and said adjustment manipulating member,
wherein said adjustment manipulating member moving forward in the direction in which said adjustment manipulating member is pulled out is elastically biased in a direction of the backward motion by said conical coil spring.

15. A controller according to claim 1,
wherein said adjustment operating member comprises a first adjustment operating member arranged in said housing mechanism, and a second adjustment operating member arranged in said housing mechanism,
said first adjustment operating member is configured to pivot by the pivoting operation of said adjustment manipulating member, thereby pivoting said second adjustment operating member, and
said second adjustment operating member operates by the pivotal motion to adjust the elastic biasing force of said elastic biasing means.

16. A controller according to claim 15,
wherein said adjustment manipulating member is an adjustment manipulating cap, and
said adjustment manipulating cap is substantially put on a head of said first adjustment operating member.

17. A controller according to claim 1,
wherein said adjustment manipulating member comprises a first pivotal-motion-transmitting engaging portion,
said adjustment operating member comprises a second pivotal-motion-transmitting engaging portion, and
when said adjustment manipulating member is in a backward-motion position in which said adjustment manipulating member moves backward to said adjustment operating member, said first pivotal-motion-transmitting engaging portion of said adjustment manipulating member and said second pivotal-motion-transmitting engaging portion of said adjustment operating member are disengaged, and said adjustment operating member does not operate even when said adjustment manipulating member pivots by the pivoting operation of said adjustment manipulating member, and, when said adjustment manipulating member is pulled out from the backward-motion position with respect to said adjustment operating member, said first pivotal-motion-transmitting engaging portion and said second pivotal-motion-transmitting engaging portion engage with each other, thereby transmitting the pivoting operation of said adjustment manipulating member to said adjustment operating member and operating said adjustment operating member.

18. A controller according to claim 1,
wherein an opening communicating with the third vent hole is formed in a top-surface portion of said adjustment manipulating member.

19. An artificial respirator configured to control a gas pressure by a pressure controller,
said pressure controller comprising:
a housing mechanism which has a first vent hole, a second vent hole and a third vent hole, and in which one of the first vent hole and the second vent hole is configured to be used as an inlet of an inspiratory gas and the other vent hole is configured to be used as an outlet of the inspiratory gas;

a control valve placed in said housing mechanism to face a gas passage between the first vent hole and the second vent hole;

elastic biasing means for elastically biasing said control valve against a valve seat formed in said housing mechanism;

an adjustment operating member to be operated to adjust an elastic biasing force of said elastic biasing means; and an adjustment manipulating member to be pivoted to operate said adjustment operating member, and said pressure controller being configured such that said control valve closes the third vent hole when a gas pressure in the gas passage is lower than a predetermined level, and said control valve opens the third vent hole such that a gas in the gas passage flows through the third vent hole when the gas pressure in the gas passage is higher than a predetermined level, wherein said adjustment operating member does not operate even when said adjustment manipulating member pivots by a pivoting operation of said adjustment manipulating member in a first state in which said adjustment manipulating member is not drawn outwardly against said adjustment operating member, and said adjustment operating member operates to adjust the elastic biasing force of said elastic biasing means when said adjustment manipulating member pivots by the pivoting operation of said adjustment manipulating member in a second state in which said adjustment manipulating member is drawn outwardly against said adjustment operating member.

20. A respirator according to claim 19, wherein said respirator further comprises a face mask including a second inspiratory gas inlet to be connected to the inspiratory gas outlet of said pressure controller, wherein both the first vent hole and the second vent hole of said pressure controller are configured to be selectively connected to the second inspiratory gas inlet of said face mask, and one of the first vent hole and the second vent hole having connected to the second inspiratory gas inlet functions as the inspiratory gas outlet of said pressure controller, and the other vent hole functions as the inspiratory gas inlet of said pressure controller.

21. A respirator according to claim 20, wherein an angle which an axis of the first vent hole of said pressure controller makes with an axis of the second vent hole is 75° to 105°.

22. A respirator according to claim 20, wherein an angle which an axis of the first vent hole of said pressure controller makes with an axis of the second vent hole is 80° to 100°.

23. A respirator according to claim 20, wherein an angle which an axis of the first vent hole of said pressure controller makes with an axis of the second vent hole is 85° to 95°.

* * * * *